US007972266B2

(12) United States Patent
Gobeyn et al.

(10) Patent No.: US 7,972,266 B2
(45) Date of Patent: Jul. 5, 2011

(54) IMAGE DATA NORMALIZATION FOR A MONITORING SYSTEM

(75) Inventors: Kevin M. Gobeyn, Honeoye Falls, NY (US); Andrew F. Kurtz, Macedon, NY (US); Donald E. Olson, Rochester, NY (US); Thomas E. Madden, Fairport, NY (US)

(73) Assignee: Eastman Kodak Company, Rochester, NY (US)

( * ) Notice: Subject to any disclaimer, the term of this patent is extended or adjusted under 35 U.S.C. 154(b) by 1078 days.

(21) Appl. No.: 11/751,652

(22) Filed: May 22, 2007

(65) Prior Publication Data

US 2008/0294017 A1 Nov. 27, 2008

(51) Int. Cl.
*A61B 5/00* (2006.01)
*G06K 9/80* (2006.01)
*H04N 5/243* (2006.01)

(52) U.S. Cl. ...... 600/301; 382/115; 382/128; 348/222.1
(58) Field of Classification Search .................. None
See application file for complete search history.

(56) References Cited

U.S. PATENT DOCUMENTS

| | | | |
|---|---|---|---|
| 5,194,955 A | 3/1993 | Yoneta et al. | |
| 5,437,278 A | 8/1995 | Wilk | |
| 5,639,151 A | 6/1997 | McNelley et al. | |
| 5,777,665 A | 7/1998 | McNelley et al. | |
| 6,154,559 A | 11/2000 | Beardsley | |
| 6,205,716 B1 | 3/2001 | Peltz | |
| 6,319,199 B1 | 11/2001 | Sheehan et al. | |
| 6,539,281 B2 | 3/2003 | Wan et al. | |
| 6,575,904 B2 | 6/2003 | Nagai et al. | |
| 6,611,206 B2 | 8/2003 | Eshelman et al. | |
| 6,927,694 B1 | 8/2005 | Smith et al. | |
| 6,968,294 B2 | 11/2005 | Gutta et al. | |
| 7,027,621 B1 * | 4/2006 | Prokoski | 382/118 |
| 7,042,486 B2 | 5/2006 | Manico et al. | |

(Continued)

FOREIGN PATENT DOCUMENTS

| WO | 01/71636 | 9/2001 |
|---|---|---|
| WO | 2005/006969 | 9/2005 |

OTHER PUBLICATIONS

R.R. Anderson, Polarized Light Examination and Photography of the Skin, Archives of Dermatology, vol. 127, pp. 1000-1005 1991.

(Continued)

*Primary Examiner* — Eric F Winakur
*Assistant Examiner* — Bobby Soriano
(74) *Attorney, Agent, or Firm* — Raymond L. Owens

(57) ABSTRACT

A method for providing normalized physiological monitoring data of an individual with a measure of the quality of the normalization, including providing a reference feature based on a physiological attribute of the individual for which an attribute value can be determined; unobtrusively capturing physiological monitoring data for the individual during a series of capture events and determining the capture conditions present during each capture event; detecting the presence of the reference feature in the series of captured physiological monitoring data and determining associated attribute values for each capture event; normalizing the captured physiological monitoring data from each capture event according to differences in the attribute values associated with each event and previously calculated attribute values; and calculating normalization confidence values for the individual at the series of capture events, based on capture conditions, normalization transforms, or semantic data, wherein the confidence values statistically measure the quality of the normalization.

17 Claims, 12 Drawing Sheets

U.S. PATENT DOCUMENTS

| | | |
|---|---|---|
| 7,058,209 B2 | 6/2006 | Chen et al. |
| 2003/0069752 A1 | 4/2003 | LeDain et al. |
| 2005/0175218 A1 | 8/2005 | Vertegaal et al. |
| 2005/0228245 A1 | 10/2005 | Quy |
| 2006/0058694 A1 | 3/2006 | Clark et al. |
| 2006/0149140 A1 | 7/2006 | Eldridge |
| 2007/0085690 A1 | 4/2007 | Tran |
| 2008/0077001 A1* | 3/2008 | Ruscio et al. .................. 600/407 |
| 2009/0059028 A1* | 3/2009 | Kollias et al. .............. 348/222.1 |

OTHER PUBLICATIONS

N Tsumura et al, Image-based skin color and texture analysis/synthesis by extracting hemoglobin and melanin information in the skin, Proc. ACM Transactions on Graphics, SIGGRAPH 2003.

C. J. Harland et al, Electric potential probes—new directions in the remove sensing of the human body, Meas. Sci. Technol. 13, pp. 163-169, 2002.

Tapia et al, Activity Recognition in the Home Using Simple and Ubiquitous Sensors, Proc. of Pervasive 2004, vol. LNCS 3001, pp. 158-175 2004.

G. Aggarwal et al, A System Identification Approach for Video-Based Face Recognition, Proc. of the International Conf. on Pattern Recognition, Aug. 23-26, 2006, Cambridge UK.

Phillips brochure—Intelligent Personal-Care Environment—the bathroom cares for you, 2002.

* cited by examiner

IMAGE DATA NORMALIZATION FOR A MONITORING SYSTEM

CROSS REFERENCE TO RELATED APPLICATIONS

Reference is made to commonly assigned U.S. patent application Ser. No. 11/555,822, filed Nov. 2, 2006, entitled "An Integrated Display Having Multiple Capture Devices", by Kurtz et al, U.S. patent application Ser. No. 11/751,645 filed concurrently herewith, entitled "Monitoring Physiological Conditions" by Kurtz et al, U.S. patent application Ser. No. 11/751,646 filed concurrently herewith, entitled "Establishing Baseline Data for Physiological Monitoring System" by Gobeyn et al, U.S. patent application Ser. No. 11/751,648 filed concurrently herewith, entitled "Capturing Data for Individual Physiological Monitoring" by Kurtz et al, U.S. patent application Ser. No. 11/751,657 filed concurrently herewith, entitled "Inferring Wellness from Physiological Condition Data" by Gobeyn et al and U.S. patent application Ser. No. 11/751,660 filed concurrently herewith, entitled "Privacy Management for Well-Being Monitoring" by Kurtz et al, the disclosures of which are incorporated herein.

FIELD OF THE INVENTION

The present invention relates to monitoring the physiological conditions of one or more individuals in an unobtrusive ongoing manner, by using images acquired by one or more digital capture devices.

BACKGROUND OF THE INVENTION

In many places worldwide, population demographics point persuasively towards a gradually emerging mismatch between the need for medical care among aging populations, and the number of health care providers available to respond to the need. There are many proposals, from increased training of medical professionals, to telemedicine, and electronic patient records, which may satisfy the needs to an extent. Telemedicine can fulfill an immediate need for consultation by a remotely located physician or specialist. Telemedicine could also be applied to the monitoring of slowly evolving medical conditions, such as chronic wounds or infections. However, there is certainly room for a multiplicity of solutions.

As a parallel and interacting societal and cultural trend, the Internet is enabling families and individuals to have greater influence on their own health and well being, as health and medical information has become increasingly accessible. However, in many instances, significant time can pass during which subtle physiological changes can be occurring to an individual without their awareness. Alternately, individuals can be aware of a more obvious physiological change, but lack any way to quantify and confirm the change. Thus, a system or device that can detect, quantify, and track physiological changes would have significant utility. Examples of such physiological conditions might include changes in nutrition, weight gain or loss, and emotional state. As a further capability, the aforementioned device could have the capability to alert an individual, family members, and their health care provider(s) to detected changes. The system could also interact with a database to screen and tentatively identify relevant medical conditions.

As can be seen, a device or system with aforementioned attributes would have considerable value. To realize this value, such a system or device should be sufficiently inexpensive to be consumer accessible. The system should also have attributes, such as multi-functionality, autonomous operation, ease of use, and perhaps portability, to have it function as a natural part of the consumer or home environment. It should operate unobtrusively, collecting useful data while reducing its interaction requirements and maintaining user privacy. Preferably it can be useful for tracking a broad range of physiologic conditions (such as nutrition, weight, or posture, for example), some medical conditions, and have cosmetic applications as well. Likewise, the system should be sufficiently flexible to function properly for different individuals (such as different family members), and be able to accommodate ethnic, seasonal, and cultural differences. Such a system might be expected to be imaging based, but also accept other sensory inputs. A system with these features would enable many individuals to address their health and well-being issues more pro-actively.

There are prior art systems that consider some of the issues described above. As a first example, U.S. Pat. No. 5,437,278 by Wilk describes a medical diagnostic system that collects medical data from an imaging system or from a physiological measurement device. The Wilk '278 system attempts to automate medical data collection and diagnosis. For example, video image data is collected, and these images and related imaging parameters are compared to a master database to facilitate medical diagnosis. The collected images are also compared to prior scanned patient data to facilitate ongoing patient monitoring. Although it is strongly implied, rather than explicitly stated, the Wilk '278 system is targeted for use in clinical environment. For one, the system of Wilk '278 is to be operated by a health care professional or an unskilled aide. Wilk '278 also anticipates that the imaging device can be a video camera, an X-ray machine, an MRI scanner, or a CAT scanner. The system is also intended to accept inputs from EEG and EKG machines and other monitoring devices. As can be seen, Wilk '278 employs expensive medical machinery that is expected to be in a hospital or clinic, and not in a home. Thus Wilk '278 does not propose a system for monitoring physiological conditions that is applicable to the home environment.

As another example, U.S. Patent Application Publication No. 2006/0149140 by Eldridge provides a diagnostic and treatment system for patient diagnosis and crisis management. The described system accepts a variety of inputs, including video, sound, speech recognition, and sensor signals. However, the system application is targeted towards a medical crisis type environment, such as an emergency room, where it will integrate inputs from various devices and output diagnosis and treatment information. While some consulting doctors may be remotely located, some health care professionals are present to operate the system and treat the patient. Thus, again, the Eldridge '140 system does not propose a monitoring system for physiologic conditions applicable to the home environment. Specifically, it can be seen that neither Wilk '278 nor Eldridge '140 anticipate an unobtrusive privacy-maintaining system capable of ongoing, day after day, monitoring of multiple individuals. Additionally, neither system provides image normalization to reduce the variability associated with capturing images of different individuals, under a variety of lighting conditions, taking into account seasonal changes, and other factors that would be common to capture in a home environment.

The general need for physiological monitoring of individuals outside the typical clinical environment is known. For example, U.S. Pat. No. 6,205,716 by Peltz describes a modular portable video-conferencing enclosure or kiosk for facilitating remote telemedicine. However, the apparatus of Peltz '716 is intended to be equipped with sophisticated equipment to perform ECGs and EEG, and other tests, thus enabling telecardiology, telesurgery, and other kinds of direct medical care. The Peltz '716 system can be as expansive as a flatbed truck and is clearly not intended for common-day residential use.

As another non-clinical application, the prior art includes patents such as U.S. Pat. No. 6,927,694 by Smith et al., which describe camera-based systems which image facial features to enable assessment of the potential fatigue of a driver of a vehicle. Such systems can assess driver drowsiness relative to various physiological parameters, including eye blink, head movement, facial expression, yawning, while operating under a range of illumination conditions. However, these driver fatigue assessment systems are not used to assess the well-being or health of one or more individuals in a residential environment. Thus, these systems do not anticipate the issues (including managing privacy, unobtrusive image capture, image normalization), the opportunities, or the design of a residential family well-being monitoring system.

Other patents, such as U.S. Pat. No. 6,611,206 by Eshelman et al., and U.S. Pat. No. 6,968,294 by Gutta et al., anticipate the need for home health monitoring of individuals, such as the elderly, who would normally need a caretaker to protect their health. The monitoring systems of these patents includes a pervasive array of sensors, including cameras, to enable monitoring of the subject relative to behavior, emotional state, activity, safety, environment, and security. These systems also include devices to provide local or remote alerts concerning the subject and his or her environment. The systems of Eshelman '206 and Gutta '294 are neither unobtrusive nor intended for generalized family health care. Additionally, these systems really do not provide imaging-based health assessments for multiple individuals that address the variability that would be expected, including variations in age, ethnicity, ambient lighting conditions, seasonally induced changes in appearance, privacy, health history, and other factors.

Another patent, U.S. Pat. No. 6,539,281 by Wan et al., provides for a medicine cabinet or similar device that assists users in selecting, taking, and tracking their use of medications. In this instance, the medications are provided with radio frequency identification tags, and the medicine cabinet is equipped with a radio frequency tag reader. A touch screen flat panel display can be provided with the cabinet, as an interface to the users. The cabinet may include a camera and face recognition software, to enable user identification. While the intelligent medicine cabinet of Wan '281 is useful, it does not use a camera for assessing the physiological state or conditions of the users, and as such, it does not anticipate either the issues or opportunities that arise from such considerations.

There are other health care devices that are more focused on the home monitoring of health or medical parameters, rather than general behavior and activity. As an example, international patent publication WO2001/071636 by O'Young describes a personalized health profiling system intended to collect quantitative health data on individuals in their home environments, so as to look for warning signs of potential disease or a changes in one's health or physical state. The data collection is intended to be sufficiently unobtrusive that it can be undertaken during normal daily activities, such as working, sleeping, or exercising. In particular, O'Young '636 anticipates that one or more sensors are to be worn by an individual proximate to their body, to monitor heart rate, blood oxygenation, gait rhythm, or body temperature. Similarly, international patent publication WO2005/006969 by Montvay et al. anticipates a health monitoring system that enables health related-coaching of an individual who may be in their own home. This system can have sensors that are worn by an individual, or implanted in their body. Such sensors can monitor the electrocardiogram (EGG) or a respiration rate of the individual. Other sensors can be provided, for example mounted to a wall, to monitor environmental data, like air temperature, humidity, and other parameters. While the devices and systems of O'Young '636 and Montvay '969 are targeted for home health care, they are not targeted for generalized family health care. In particular, they do not anticipate an unobtrusive system capable of ongoing, day after day, monitoring of multiple individuals. Additionally, none of these systems provides image normalization to account for the variability associated with multiple individuals, lighting conditions, seasonal changes, and other factors.

The system of U.S. Patent Application Publication No. 2003/0069752 by LeDain et al. has greater comparative relevance, as imaging is a key aspect of the described home health-care system. LeDain '752 anticipates a home health care system to facilitate medical care and monitoring for an individual by a health care clinician, where the clinician can be present or located remotely. To enable remote care, the individual of interest would possess an equipped medical kit, a teleconferencing camera, and a gateway computer for data transfer. The medical kit can be equipped with various medical devices to measure vital signs, such as a blood glucose meter, a blood pressure measurement device, a blood oxygenation sensor, or an ECG module. On the occasions that a clinician is not present, the individual would use these devices, following instructions provided by the gateway computer. The video camera enables real-time teleconferencing between the individual and a clinician. It also enables a clinician to record events from a visit to the individual's residence. Ultimately, a medical professional can use the video images to assess the physical condition and the behavioral indicators of the individual in question. Provision is made to unobtrusively hide the video camera within a picture frame behind a photograph. However, the photo is then deliberately removed when the camera is used for video capture.

The system of U.S. Patent Application Publication No. 2005/0228245 by Quy, uses a similar home health care system to that of LeDain '752. In Quy '245, a user is provided with a health-monitoring device that communicates to remote locations through a cell-phone wireless device (such as a PDA) to a remotely located caregiver or clinician. The health monitoring device can have one or more modules or sensors for measuring health attributes such as blood glucose or oxygenation levels, blood pressure and heart rate, respiration, temperature, or exercise performance, of a human subject. A camera, which can be a separate monitoring device, or integral with the wireless communication device, can be provided to collect visual image data via still or video electronic photography.

Although the systems of LeDain '752 and Quy '245 describe home health care monitoring systems that involve imaging, in these systems, the health care monitoring is intended for a previously identified subject or patient. In particular, patients who are being monitored for a variety of conditions can be sent home with a PC-based or network-based telemedicine appliance that can be used to connect them back to a hospital or doctor's office via ISDN, DSL or cable modem connections. Additionally, these systems employ a range of biomedical sensors, which typically require physical contact to function, and where imaging is only a secondary component.

SUMMARY OF THE INVENTION

By normalizing captured physiological monitoring data improved confidence values are produced. In another aspect the sclera of an individual's eye is effectively used in the normalization process.

Thus, the present invention is generally useful for aiding individual monitoring and assessment of general well being and health. The present invention functions unobtrusively, perhaps on a daily basis, with consideration for privacy, while enabling monitoring of one or more individuals. The system enables assessment of a wide range of general physiological conditions, which can be used within the family setting, or shared within a family's social network or with medical professionals, as seems appropriate.

Monitoring is enabled by the use of semantic data and by image normalization and data assessment to generate robust image content and physiological metrics. These data can be shared immediately or remotely, and conveyed by a variety of techniques.

BRIEF DESCRIPTION OF THE DRAWINGS

In the detailed description of the preferred embodiments of the invention presented below, reference is made to the accompanying drawings in which:

FIG. 2b is a cross-sectional illustration of a portion of FIG. 2a;

DETAILED DESCRIPTION OF THE INVENTION

The apparatus and method of the present invention addresses the need for a system for monitoring physiological conditions, which includes technologies to acquire physiological data over time, analyze the data to provide wellness assessments, validate the data and test the assessments, and provide assessments to the users. The system can include an integrated display and image capture device. The key functional attributes of the system include the following:

It provides day after day ongoing access in an unobtrusive way, targeted for the home environment.

It is designed with consideration for family privacy issues.

It is enabled by identification of individual users (user provided, face recognition, audio recognition, for example)

It can be adapted to provide monitoring and assessments for new individuals or new conditions.

It can use an integrated capture & display device, which can use more than just visible light.

It is primarily used as an imaging system to collect facial images, although it can be used to collect images of other body regions, or can be used indirectly via peripherals or accessories.

It normalizes collected images for different individuals and takes into account changes in appearance such as might happen seasonally (for example tanning).

It compiles assessments of physiological conditions or changes.

It can provide or enable assessments of multiple individuals.

It provides alerts, stores data, and enables data access.

Figure 1:
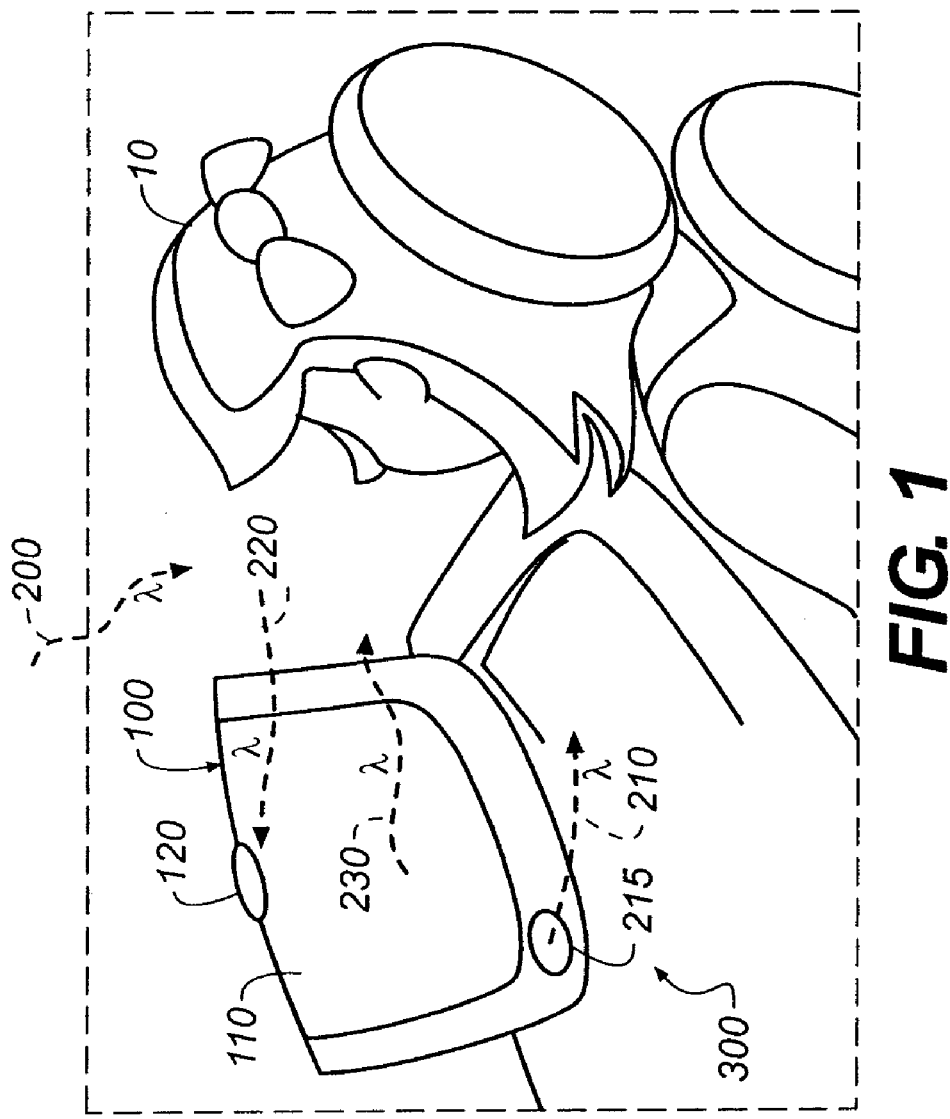
FIG. 1 shows a perspective of a user of the present invention interacting with a system capable of providing the present invention.

The basic functionality of the hardware portion of physiological monitoring system 300 is shown in FIG. 1, wherein a user 10 faces an electronic imaging device 100. Generally speaking, electronic imaging device 100 provides image capture, and can provide image and data display, or both image capture and image and data display. In the instance of FIG. 1, electronic imaging device 100 is illustrated as a "display that sees" device that includes both an image display 110 and one or more cameras 120. The display 110 can be a computer display (desk-top or laptop), a television, an electronic book, or other electronic display device. As a particular example, electronic imaging device 100 can include a computer equipped with a video camera, which can be a web-camera. Web-cams are commercially available from numerous companies, including Creative Laboratories (Singapore) and Logitech (Switzerland). As shown in FIG. 1, electronic imaging device 100 provides an output of display light 230 from display 110 in the direction of user 10. Ambient light 200, which can be natural lighting or room lighting also illuminates user 10. A portion of this light becomes capture light 220, which is collected by camera 120 and focused by a lens (not shown) onto an internal sensor array (not shown). If the ambient light 200 is insufficient or sub-standard electronic imaging device 100 can supply illumination light 210 from an illumination light source 215 to illuminate user 10.

Figure 2A:
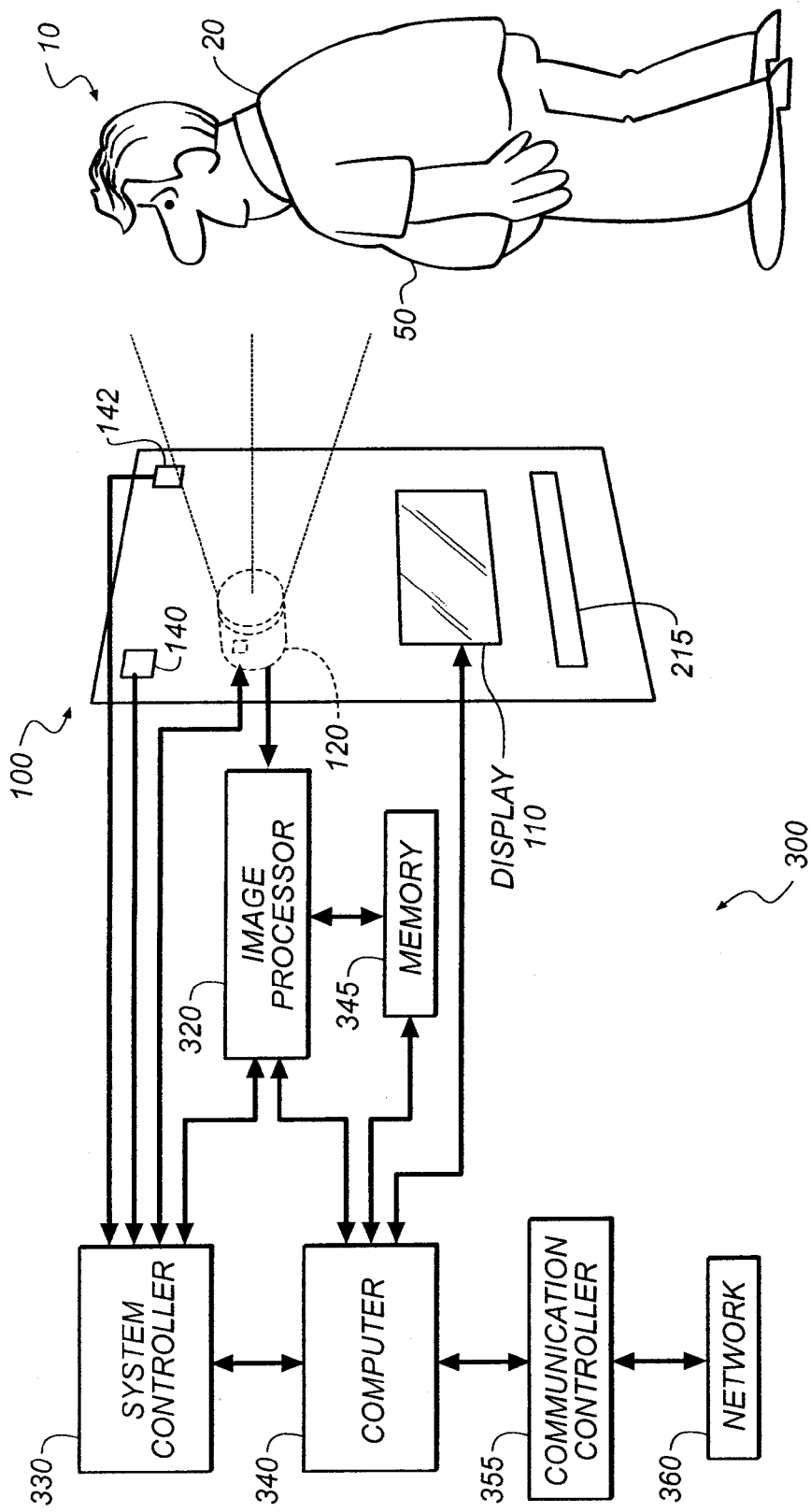
FIG. 2a shows an illustration depicting the primary elements of the present invention.

In a broader context, the hardware for physiological monitoring system 300 can be understood via FIG. 2a. The primary elements of physiological monitoring system 300 are the electronic imaging device 100, which includes at least one camera 120, and possibly a display 110. Electronic imaging device 100 is interconnected to image processing electronics 320, a system controller 330, a computer 340, memory or data storage 345, a communications controller 355, and a network 360. The image processing electronics 320 potentially serve multiple purposes, including improving the quality of image capture of the camera 120 associated with a local electronic imaging device 100, improving the quality of images displayed at a local display 110, and processing the captured images to aid the derivation of metrics relative to physiological conditions. Computer 340 coordinates control of the image processing electronics 320 and system controller 330. Computer 340 also manipulates and accesses data from memory 345, display 110, image processing electronics 320, and network 360. Both image processing electronics 320 and computer 340 can access various databases (which will be discussed subsequently), many of which are stored in memory 345. System controller provides various control and driver functions for a local electronic imaging device 100, including display driver and image capture control functions. A variety of detectors can be provided, including an ambient light detector 140, a motion detector 142, and various secondary detectors 144 that can be used for measuring ambient light or other physiological or environmental parameters. These detectors are interconnected with computer 340 or controller 330. Communication controller 355 acts as interface to a communication channel, such as a wireless or wired network 360, for transferring image and other data from one site to the other.

As noted previously, the principal anticipated application of physiological monitoring system 300 is in the residential market. Yet unfulfilled needs can be identified from a purely medical perspective and from a broader context of human well-being and health. The newspaper, USA Today, reports that the United States could have a shortage of 85,000 to 200,000 doctors in 2020, fueled not only by malpractice insurance and other non-medical business issues impacting the numbers of students who go into medicine, but also by 79 million baby boomers reaching retirement age and needing more medical care. Further, decreasing contributions towards health care from employers and governmental entities will mean that consumers will pay much more for health care. These pressures will likely force increasing health care expenses upon consumers, which might be somewhat ameliorated if consumers can better assess if and when intervention by health care professionals is warranted.

Undeniably, the doctor shortages, the increased needs of baby boomers, and the diminishing contributions made by innumerable employers means that consumers increasingly have to take greater control over their own and their family's health care. Significant care for acute conditions will likely be shouldered by the "sandwich generation", i.e., almost 3 in 10 of those aged 45 to 64 with children in the home, who are also caring for a senior, according to a study based on the 2002 General Social Survey. And many of those parents who do not have their own elderly parents living in their homes are still anxious about their elderly parent's health, especially when the elderly live in distant locales.

The US health care system is primarily one of "break-fix". A consumer gets a condition or a disease, and then the health care system treats it. In fact, the majority of the health care budget is spent once patients have become very ill. Relatively little health care money is allocated to very early detection of deteriorating or changing conditions.

In that regard then, consumers, whether at an individual or family level, would be advantaged by a system that enables ongoing physiologic monitoring. Consider the relevant example that "Mom" would benefit by tools that enable her to track the well-being and health of her kids and parents at home (or at her parents' distant home). Such a system would increase her chances of noticing disease early, or other conditions (such as excessive cold or heat) that could lead to illness or disease. Although "Mom" will not likely have devices at her disposal that require substantial medical training to use and to interpret (such as X-Ray or heart monitoring devices), any tools that help her discover the symptoms or evidence of a significant physiological change that has occurred would have considerable value to her.

In particular, a range of physiological conditions or changes related to general well-being or health, such as nutrition, posture, weight, lack of sleep, and emotional state, might be assessed from a visual (image based) record. Likewise, a range of medical conditions, or the symptoms thereof, might be identified (including neurological conditions or circulatory problems) from a visual record. Additionally, physiological changes for an individual relative to a range of medical conditions (such as diabetes, heart conditions, or chronic wounds) might be monitored or documented with a visual record. Significantly, the physiological monitoring system 300 is intended to enable the acquisition of a longitudinal record of image and image-derived data. As a result, the system 300 can document, and perhaps identify, changes in physiological conditions that might evolve slowly and occur with little awareness. Thus, "Mom" could apply her parental instincts, supplemented by both past and present data, to determine if enough change has taken place to warrant intervention by medical professionals. These data can enable "Mom" to reach health related assessments through various intermediate steps, such as consulting with Internet databases, her social network of family and friends, and other reference points, that may reduce the need to consult with medical professionals.

The study of the visual properties of skin is well known in the computer graphics field where it is important to understand the effects of aging and environmental factors on the way a person looks to be able to produce an accurate simulated image of a person. This can be important in modifying an image to simulate the effects of aging on a person as an example. An exemplary article that shows a variety of effects to the way a person looks under different lighting conditions for the application of computer graphics is contained in the article by N. Tsumura et al, "*Image-based skin color and texture analysis/synthesis by extracting hemoglobin and melanin information in the skin*", Proc. ACM Transactions on Graphics, SIGGRAPH 2003. While the visual properties of skin have been studied, the automated monitoring of a person's visual attributes over time for the purpose of tracking changes in health has not been suggested.

The aforementioned longitudinal record of physiological data is a potential input for medical assessment that is seldom available today. As people go about living their daily lives, a given individual or family member, can be unaware of a physiological change until a crisis occurs. For example, parents can miss a daughter's developing anorexia until it is evidenced by extreme weight loss and skin color changes. However, the accumulation of an ongoing longitudinal record, supplemented by an assessment technique, will document and pro-actively help to identify, evolving physiological changes. Although system 300 can obtain data on a daily basis, many wellness parameters 410 will generally change very slowly, and thus some wellness data can be measured and retained on a less frequent basis. For example, as physical attributes such as weight or posture tend to change slowly, the associated wellness parameters can be sought or retained on a weekly, monthly, or quarterly basis, depending on the attribute or trait in question and the variability associated with its measurement.

Thus, the system 300 is intended to enable the collection of a record of physiological data for one or more individuals. To enable this, the system 300 is provided with a dual-purpose device, and in particular an electronic imaging device 100 that unobtrusively captures images of a user or subject via one or more cameras 120. Electronic imaging device 100 can be a computer monitor, television, cell phone, mirror, or other display that sees the subject (with a camera 120) while the subject (user 10) is looking into the device. As shown in FIG. 1, electronic imaging device 100 is a computer, such as desktop or laptop system. The camera 120 can be mounted at the display edge (as shown), or be integrated into electronic imaging device 100, such that it looks through the display 110 at a user 10. Whereas, the electronic imaging device 100 shown in FIGS. 2a and 2b includes a mirror 136 integrated with a camera 120 and (optionally) a display 110. A camera 120 typically includes an imaging lens 122 that provides an image onto an image sensor array 124, through a spectral filter 126. In this case, camera 120 can look through an aperture A, for example provided by a semi-transparent mirror 134. To aid in hiding the camera 120 and aperture A, semi-transparent mirror 134 can have a gradient reflectance, with the lowest reflectance in the center of aperture A. The semi-transparent mirror 134 can also be a flickering device that is driven electronically to switch between reflecting and transmitting states. Alternately aperture A can be an optical pinhole (<0.5 mm diameter), making camera 120 a pinhole camera. In any case, cameras 120 are preferably hidden within device 100, and not generally visible to the users. As shown in FIG. 3, physiological monitoring system 300 can be networked, and utilize several electronic imaging devices 100 within a residence, including both the computer monitor and mirror types. In principal, the intention is that the physiological images are unobtrusively collected while the subject or subjects look into the mirror or display, which they are already doing to view themselves, or to view information, communications, or entertainment. These captured images can be acquired day after day, month after month, and year after year, resulting in a rich image-based representation of the subjects over long periods of time.

Although the configuration of physiological monitoring system 300 as a distributed network is particularly advantageous relative to capturing physiological image based data for multiple family members, various issues regarding individual and family privacy are accentuated. In particular, placement of electronic imaging devices 100 as one or more bathroom mirrors is advantageous relative to the image capturing. For example, in a household, a mirror type electronic imaging device 100 can be provided in the master bathroom, while another can be provided in a children's bathroom. Considering human behavioral patterns involving personal grooming, the best opportunity for capturing image data on a day after day basis could be from the mirror type electronic imaging devices 100. Also, the most repeatable, and perhaps the best, set of illumination conditions might be found in the bathroom setting. However, as can then be anticipated, management of user privacy, particularly in the bathroom setting, is very important. On the other hand, electronic imaging devices 100 that are integrated into a computer, television, or entertainment station would be expected to see regular usage on a daily basis, or nearly so, depending on the household. Although the privacy concerns related to image capture from these non-bathroom located devices might be reduced, the image capture conditions may be both inferior and more variable. In any case, various hardware and software design features can be integrated into physiological monitoring system 300 to address privacy concerns and any associated variability inherent in the capture conditions.

Notably, it is not sufficient to simply capture an image, but image assessment, enabled by image normalization, is key. Again, considering a home environment, the appearance of family members can vary significantly relative to gender, age, skin color, hair color, height, weight, and other factors. Likewise, the basic appearance of any individual can vary by season (such as tanned or sun-burnt), by behavior (including use of cosmetics, exercise, or alcohol and drug use or abuse), and by other factors. The ambient lighting can also change dramatically from one image capture opportunity to the next. In a similar fashion, the position of an individual relative to the image capture device can lead to variation in the size, orientation, or placement of the individual in the captured image. Therefore, to compensate for these wide ranges of variables that can affect image capture and interpretation with unobtrusive image capture, the process of physiological monitoring employs an image normalization process 500 to decrease the impact of the capture variables. In particular, the capture step is followed by the image normalization process 500, which modifies the captured imagery before size or color-based wellness parameters are derived from the image data. Processes for assessing physiological conditions of the subjects then follow the data normalization process. Likewise, these processes for assessing or inferring a subject's well-being must account for subject variability relative to appearance, behavior, privacy, and other factors.

Figure 4:
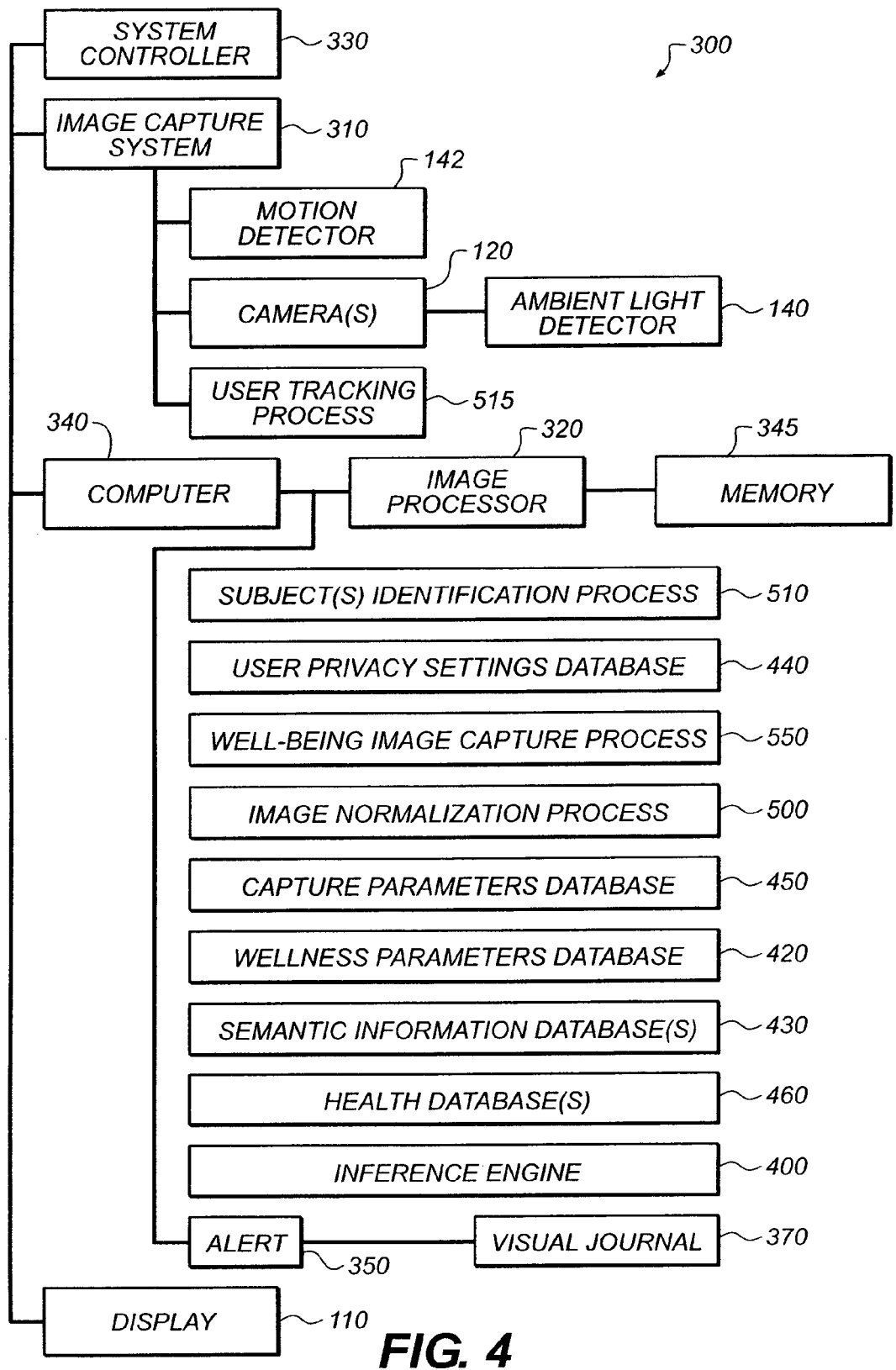
FIG. 4 is a block diagram depicting the primary operational elements of the present invention.

As then can be seen, FIG. 4, which is a block diagram, and FIGS. 5a-d which are flow diagrams, together illustrate in greater detail the operational considerations and logic of the physiological monitoring system 300 of the present invention. FIG. 4 particularly illustrates many of the data processing functions that are realized through an interaction of the computer 340, image processing 320, and memory 345, while FIG. 5a generally illustrates the overall operational processes that the system steps through when in use. As an example, physiological monitoring system 300 can be operating according to an internal clock (not shown), such that it is shut off at night and then operates in a low energy consuming watchful state during the day.

Camera 120, ambient light detector 140, motion detector 142, and user tracking process 515 together include an image capture system 310, which are used in a coordinated for image capture of subjects 10. As a motion detector 142 senses that a potential subject (step 512) has entered the operational range of an electronic imaging device 100 located in a particular place within a residence, an initial image capture process 540 is engaged. Motion detector 142 can include a sound sensor (microphone), a light intensity sensor (including a near-IR sensor), or an optical sensor that detects motion, or a combination thereof. Camera 120 can also support the motion detection function, for example using image area histograms to detect presence and position. A user tracking process 515, which can employ a motion detector 142 and cameras 120, then tracks the location of the potential subject relative to the electronic imaging device 100. When physiological monitoring system 300 determines that a potential subject has entered the field of view of a camera 120, an initial image capture process 540 would cause camera 120 to acquire an initial image, with assistance from the user tracking process 515. Then using a subject identification process 510, which can access semantic identity data and can employ face recognition software, audio recognition software, or other techniques, to determine whether an individual is a known subject of interest. A good article describing face recognition techniques for video imaging is contained in the article by G. Aggarwal, A. Chowdhury, R. Chellappa, "*A System Identification Approach for Video-Based Face Recognition*", Proc. of the International Conference on Pattern Recognition, 23-26 August 2004, Cambridge, UK. If not, by default, system 300 would stop active image capture without storing any image data or starting the well-being image capture process 550. On the other hand, if an individual is identified as a known subject of interest, then the system 300 would typically proceed with the next steps in the well-being image capture process 550 for that capture event for that particular individual.

The well-being image capture process 550 is primarily a structured process for acquiring high quality images within target capture conditions for lighting, subject pose, image focus, and other parameters. Data from various databases, such as an image capture conditions database 450, a user privacy settings database 440, a semantics information database 430, and a wellness parameters database 420 is used to define the target image capture conditions for a given subject or user 10. These various types of system data, which will be subsequently discussed in greater detail, are summarized in Table 1. During the well-being image capture process 550, the physiological monitoring system 300 uses data from the privacy settings database 440 that associates subject or user identification with the desired privacy levels for that particular individual. These privacy settings can be different for various users of the system (family members). Likewise, the physiological monitoring system 300 uses data from the wellness parameters database 420 that identifies and quantifies any particular physiological conditions that are tracked for a particular individual or user 10. In a similar fashion, the semantics information database 430 can provide data concerning seasonal, cultural, behavioral, and wellness factors that can affect image capture or wellness analysis and interpretation. More generally, it should be understood that semantics is defined as the study of information related to human meaning or experience (see Table 1). Semantic information (such as events, activities, people, conditions, locations, objects, music genres) can be associated with an informational asset (such as an image, a voice record, or a data file). Finally, the physiological monitoring system 300 uses data from the capture parameters database 450 that is indicative of the preferred capture conditions for given individuals. To aid in efficient system image capture, a composite set of preferred capture conditions and images (reference images 365) for each individual can be pre-assembled from the database data, so that each database does not have to be accessed on the fly during each capture event.

TABLE 1

Primary types of system data

The privacy settings database 440 provides privacy settings that associate subject or user identification with the desired privacy levels for that individual. Exemplary privacy settings provide:

Support for identification of known subjects
Support for limiting impact on non-subjects
Access controls for lead users
Defining and associating privacy settings with individual subjects
Defining target images for various subjects
Defining image data management for privacy sensitive body regions for various subjects
Defining use of image capture alerts
Defining how assessment alerts are provided
Defining how physiological data and assessments are output, stored, and, shared
The semantics information database 430 provides semantics data, which is generally qualitative data concerning seasonal, cultural, behavioral and wellness factors that can affect image capture or wellness analysis and interpretation. Exemplary semantics data includes:

Subject identity
Familial relationships
Age, gender, ethnicity
Activities/calender - time of day, trips, vacations
Seasonal issues - such as weather, potential impact of tanning, becoming sun burnt, wind burn)
Personal behavioral factors - such as use of cosmetics or alcohol or drugs, exercise
Dietary habits, sleep habits & quality
Type of work, work habits, stress levels
Use of medications and vitamins
Reference image metrics (to support subject identification)
Special physical characteristics - for example, the presence of tattoos, war wounds, accident or sports injuries, or birth defects
Knowledge of current medical state - for example, sick, depressed, broken arm, has severe arthritis
Knowledge of personal, familial, genetic, or historical conditions - such as relatives with diabetes or cancer
Knowledge of use of medications or vitamins
The wellness parameters database 420 provides wellness parameters 410, which are principally quantitative metrics for physiological traits or conditions, which quantify various wellness, health, and medical conditions, or physical attributes. Wellness parameters can be based upon single or multi-point measurements, or temporal measurements tracking longitudinal changes. Exemplary wellness parameters 410 include:

Height, weight, body type, body-mass index
Eye color, hair color

TABLE 1-continued

Primary types of system data

Skin color (by location, averaged)
Skin texture, structure, and moisture
Skin patterning
Posture, gait
Geometry for facial features
Eye - color (whiteness) of the sclera
Eye and body movements (neurological)
Tiredness
Nutrition
Emotional state
Personal care or hygiene
Dental care
Specific to known medical conditions, such as Alzheimer's, anorexia, diabetes, acne, wounds, rashes
Specific to known personal, familial, genetic, or historical conditions
Specific to known behaviors, such as use of cosmetics
Specific to use of medications
Reference image metrics (for baseline physiological data)
Derived values; such as averages, slopes, trend-line or abrupt, longitudinal changes, frequencies, combined, confidence values
The capture parameters database 450 provides capture parameters 415 that are quantitative metrics that are indicative of the preferred capture conditions for given individuals. Types of capture parameters include:

Reference image metrics (including capture criteria for image acquisition)
Image size
Subject pose or orientation, subject distance
Camera settings (shutter speed, aperture, zoom position, focus distance)
Lighting conditions - intensity (irradiance) and spectrum (measured data or model)
Image quality - focus and resolution
Image quality - contrast & dynamic range (noise)
Image quality - still images - lack of motion blur
Geometry of facial features
Supporting data: lens focal length, lens aberration data
Composite data: using privacy, semantics, wellness, and system data that impacts capture
The image normalization process 500 derives and applies normalization or correction factors for image attributes such as color and size. Types of normalization data include:

Reference images and reference feature data or metrics (for baseline correction factors)
Normalized image data
Normalization confidence values
Normalization transforms (including for size and color correction)
White point
Color balance
Other correction factors (including for audio traits or body movement)
Other system data:

Reference images
Identification of reference features

Various system components, such as ambient light detector 140, motion detector 142, camera(s) 120, and illumination light source 215 can be used to varying extents as an aid to the well being image capture process 550. For example, the physiological monitoring system 300 can collect data from ambient light monitor 315 about both the light intensity and light spectra that can be used to enhance image capture and processing. Similarly, the user tracking process 515, which can combine face recognition software, gesture tracking, and motion tracking algorithms, can be used to watch for subject poses that are particularly conducive to a quality well-being image capture.

Figure 5A:
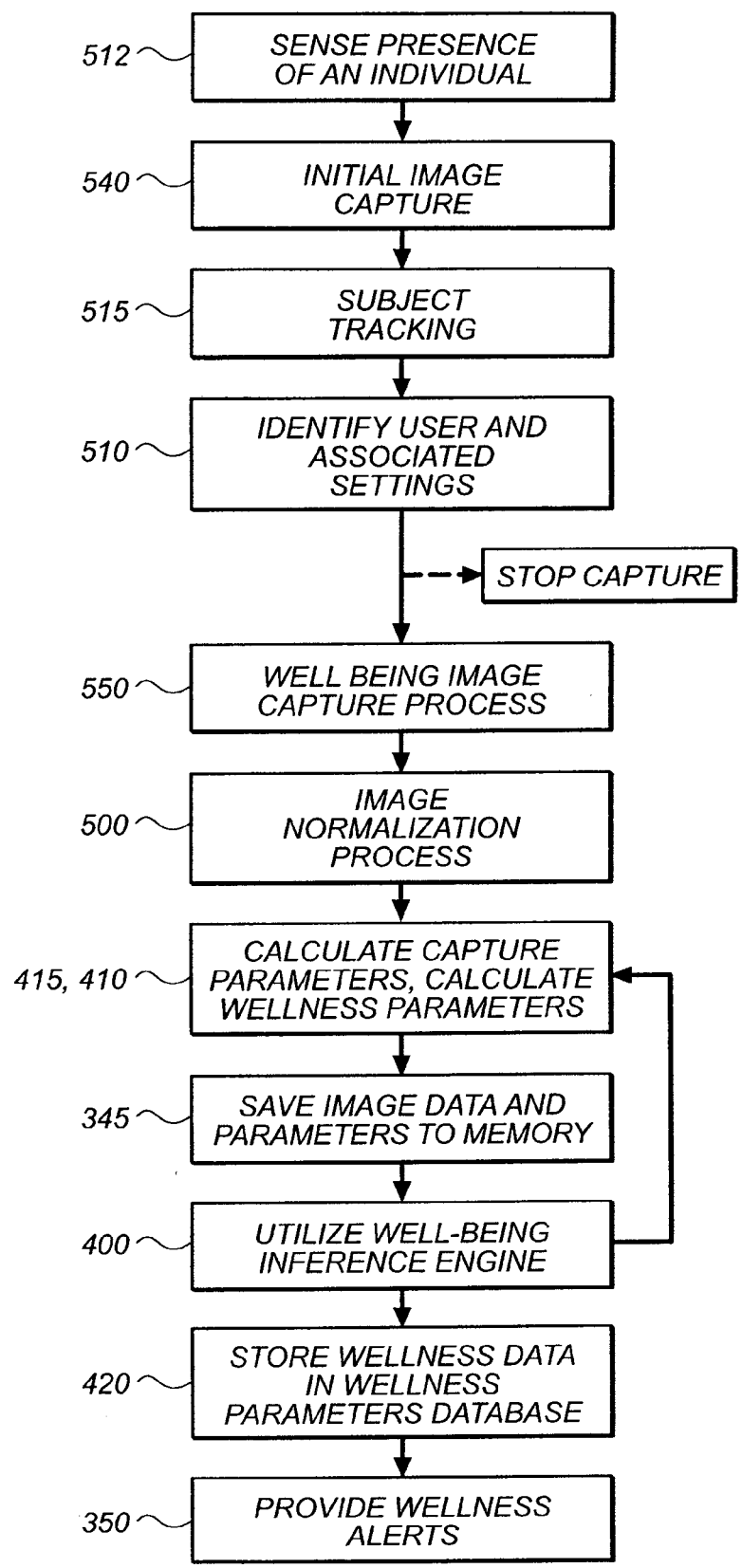
FIGS. 5a, 5b, 5c, and 5d are flow diagrams depicting aspects of the preferred operational methodology of the present invention.

Once the well-being image capture process 550 concludes a capture event with the capture of one or more images that satisfy the target conditions, the system operation progresses (see FIG. 5a) into an image normalization process or structure 500. This process step principally corrects the newly captured images for color errors and sizing errors, so that any changes that are subsequently observed in the newly captured images can be correctly attributed to physiological changes, as the variable factors of image capture are compensated for. In particular, the image normalization process 500 is tasked to overcome a number of problems that an unobtrusive system will encounter (changes in room light, distance and direction of the user from the capture device). As shown in FIG. 5*a,* the overall operational process for physiological monitoring system 300 then progresses to a step of calculating and updating wellness parameters 410 and capture parameters 415. The wellness parameters 410 are principally physiological metrics, which can be input by users 10, or derived from the image data captured by cameras 120, or calculated during subsequent analyses. Generally the wellness parameters 410 quantify various wellness, health, and medical conditions or attributes. Once these wellness parameters 410 are calculated and stored to a memory 345, an inference engine 400 (which is functionally supported by a computer 340) is utilized in the subsequent step to assess the status of physiological conditions. The inference engine 400, which can be algorithm based, or utilize artificial intelligence (AI) or learning methods, is tasked to follow and assess previously identified physiological trends for its subjects (users 10). It is also intended to look for changes, in the physiological data (wellness parameters 410), subtle or otherwise, that might be indicative of previously unidentified physiological changes. Inference engine 400 also looks to reduce errors (reduce false positives) by using a health database 460 and the semantics information database 420 to identify potential causes of apparent changes. As an example, the inference engine 400 can anticipate potential external changes that impact measured parameters that are not indicative of a real concern (e.g. skin tone—exertion level, sun and wind effects, or makeup). Should inference engine 400 conclude that a new issue or concern has arisen, there are several actions it can initiate, including providing alert signals 350 to users 10.

Approaches to meeting this challenge unobtrusively involve several key aspects. Notably, it can be expected that when a new group of users 10 first start to use a physiological monitoring system 300, that they would input various data, including user identity data, privacy preference data, wellness or health data, and semantic data into the system. The input can be via keyboard, digital cameras, photo scanners, voice, or other suitable methods. This initial input data would be appropriately assembled into the semantics database 430, the user privacy settings database 440, and as wellness parameters 410 in the wellness parameters database 420.

Figure 5B:
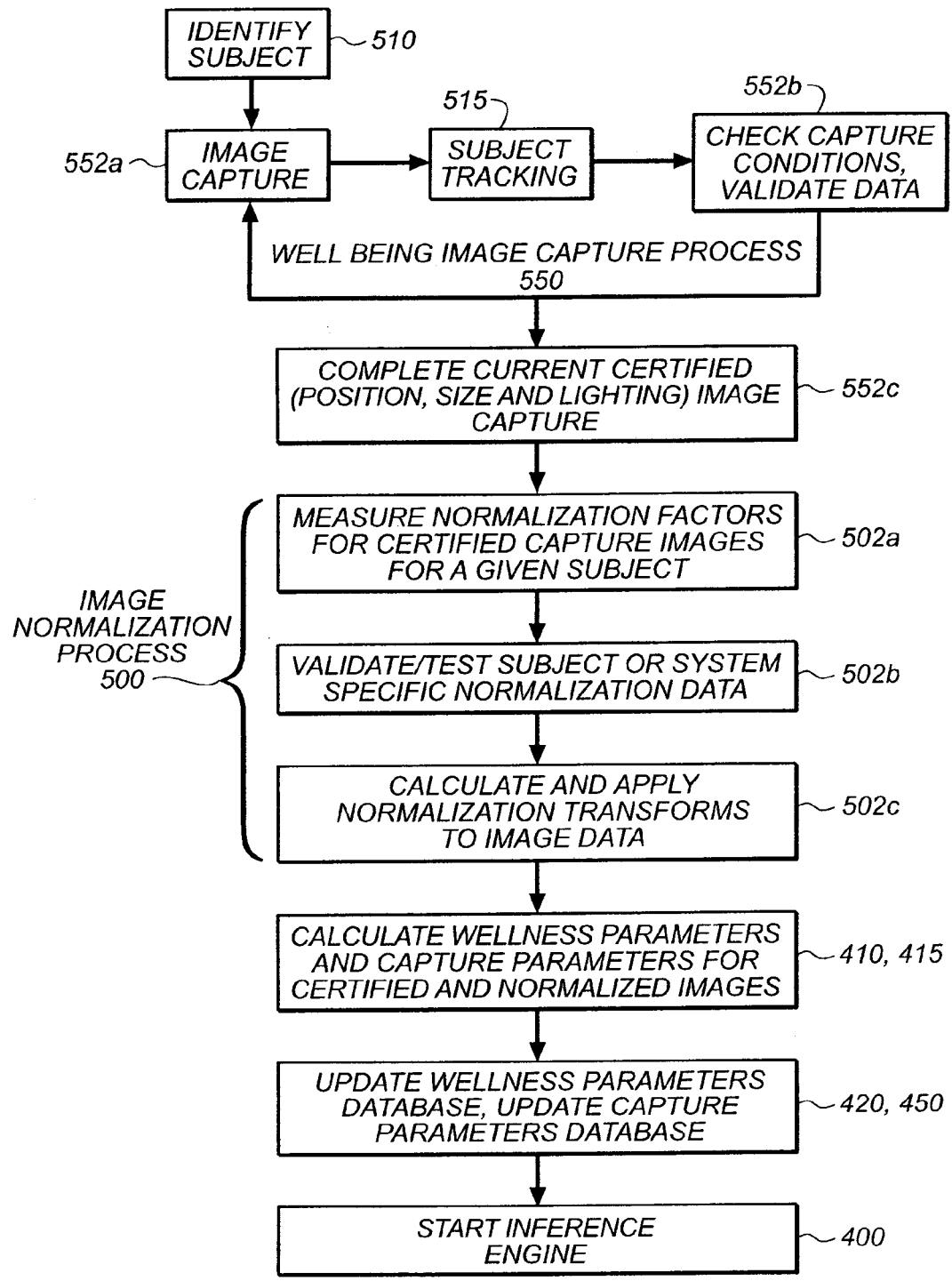
Figure 5C:
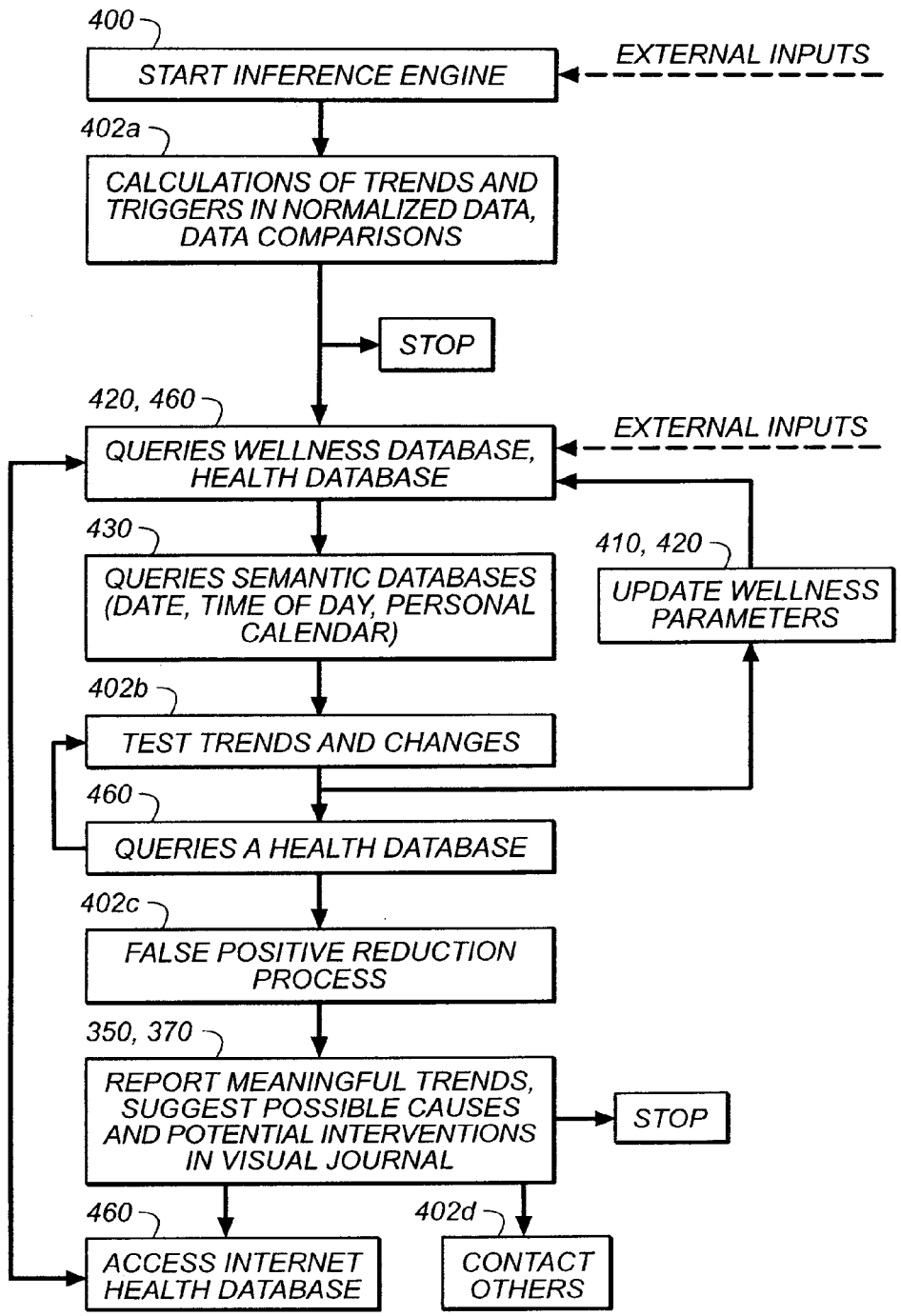
Figure 5D:
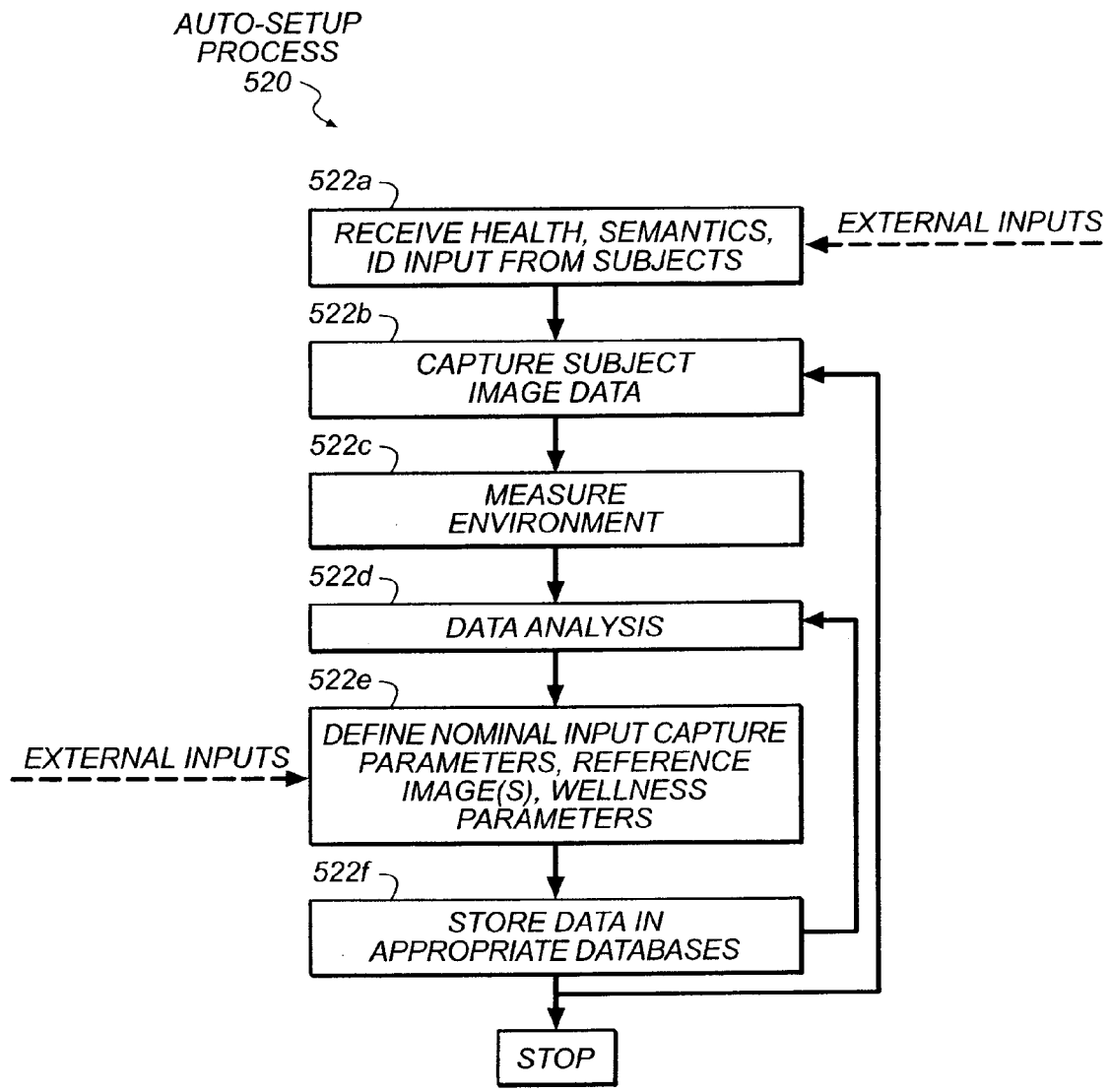

Additionally, physiological monitoring system 300 can utilize an auto-setup process 520, shown in FIG. 5*d,* to characterize control parameters for the individual users 10 under the various conditions that the system must work under (such as for different times of day, user positions in room, or room lights on or off). This process involves monitoring the users 10 (step 522*b*), as well as the user environments (step 522*c,* such as for light levels) for a suitable extended period of time (over multiple capture events) and analyzing the resulting data so that standard poses and lighting conditions can be determined for each particular individual. Step 522*b,* capturing subject image data, includes sensing an individual (step 512), initial image capture (540), subject-tracking 515, which for brevity, are not shown in FIG. 5*d*. The criteria for these capture conditions are likely determined in accordance with pre-defined guidelines (including for lighting or pose), which can account for likely variation in the color or tone of skin 40, height, weight, user pose, and other parameters that are seen in human populations. Thus, the initial input data (step 552*a*) affects this process. The resulting target capture condition criteria for each individual likely indicate a range of acceptability for each condition, rather than a unitary condition of acceptability. These target criteria quantify factors including image size, user pose, and lighting. The capture condition criteria are then expressed as capture parameters 415 in a capture parameters database 450. In effect, the auto-setup process 520 defines the preferred image capture criteria for each particular individual, which becomes the standard or baseline that the well being image capture process 550 uses in seeking to acquire quality images. The predefined capture criteria (step 522*a*) for an individual are determined by associated privacy settings, semantic data, well-being parameters, and the capture parameters, either individually or in combination. The auto-setup process 520 can accept input data (indicated by dashed lines) from external sources (steps 522*a* and 522*e*), including third party entities, which can for example, define new physiological metrics (wellness parameters 410) to be monitored.

Figure 7:
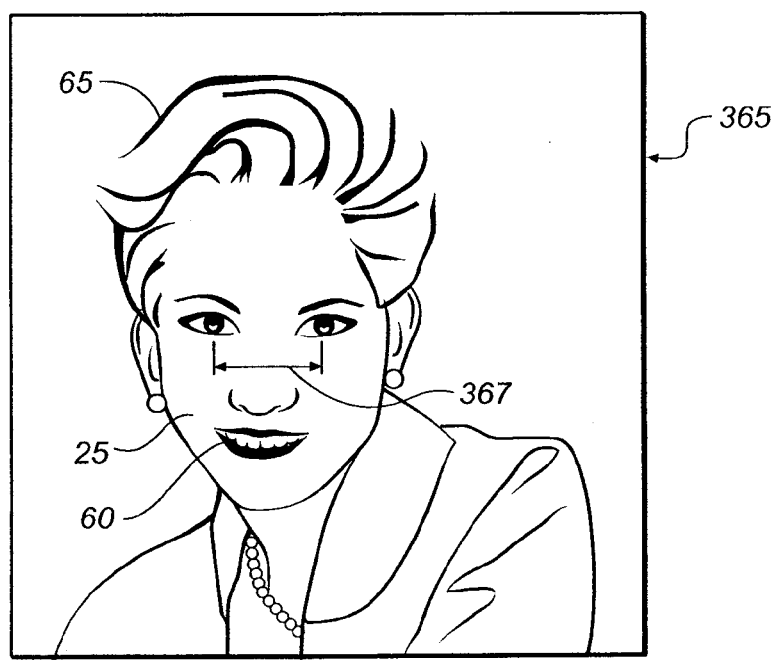
FIG. 7 is an illustration of a reference image.

The subject data and environmental data acquired during the auto-setup process is analyzed (step 522*d*) to derive target values to be used during subsequent system operation. During this auto-setup process 520, the physiological monitoring system 300 can also create one or more reference images 365 for each subject (step 522*e*). For example, most commonly, a head and shoulders image of an individuals face 25 seen direct on, will be the primary reference image (see FIG. 7). The mouth 60, hair 65, eyes 30, and other facial features should be clearly visible. Other reference images, such as direct-on views of the head and torso can be generated. The baseline reference images, and the baseline data derived from the reference images, can be established by various criteria (based on pose and lighting, for example) and can be obtained from (selectively) averaged data acquired during the duration of the auto-setup process 520. Although the reference images themselves can be stored in memory 345 as system data in step 522*f* (or as capture parameter data 415), reference image parameters (including physiological metrics) can also be derived and stored as accessible capture parameters 415 or wellness parameters 410 in the appropriate databases to aid the image capture process. The reference image parameters generally quantify physical attributes or reference features 367 of the subjects. Most reference features relate to physiological attributes that can be expected to be nominally stable or static for relatively long periods of time (such as months or years). For example, the distance between the eyes represents a reference feature 367, that when quantified, is stable in adults, but which can also be used to scale an image or to monitor the growth of a child. The reference images 365 can be broadly used by the system 300, during subject identification, well-being image capture, image normalization, well-ness assessment and inference, and wellness reporting. Facial reference images, or metrics related to reference feature 367 derived there from, can also be used as semantic data to support subject identification (via process 510).

Normalization correction factors, which can be derived from the reference images 365, and which can relate to capture parameters 415 also derived from the reference images 365, are also useful to the system 300. As an example, for the reference feature 367 of eye-to-eye distance, the associated wellness parameter 410 would contain the known physical distance, the associated capture parameters 420 would contain a range of acceptable sizes (related to subject distance) and head poses that would be suitable for a capture event, and the associated normalization correction factors would contain scaling factors, based on distance and pose to adjust newly captured images to the same scale as the reference images 365. Nominally the normalization scaling factor or transform in the case of size would be a multiplying factor to adjust the reference feature size in the image captured by the camera to equal the real physical size. In addition to obtaining baseline normalization transforms, the auto set-up process 520 can be used to acquire baseline normalization confidence values, which are statistical metrics of the quality of the normalization. The confidence values (or confidence levels) are a measure of confidence assigned to the value of an attribute (in this case, a normalization transform), which are often expressed as a percentage (0-100%) or a probability (0-1). These transforms can for example be implemented by a variety of image processing operations that can include but are not limited to point based image processing techniques such as shifts, multiplies, matrix operations, polynomial operations and single or multi-dimensional lookup tables. Of course a variety of normalization transforms may be applicable to one or more types of input data. For example, if the sounds captured are to be normalized to remove environmental factors that were present at the time of capture (such as a baby crying or a train passing) frequency based normalization may be useful. In the case that multi-spectral or non-visible data image or point data has been captured similar normalization transforms and confidence values will be calculated.

Baseline values or metrics for various other reference features 367, beyond just the eye-to-eye distance, can be established during the auto set-up process 520. For example, a baseline metric for the distance from the eye-to-eye centerline to a line crossing the upper edges of the nostrils (nares) can be measured to provide a vertical size scaling and stored as a wellness parameter 410. Baseline values for wellness parameters 410 can be established for other physiological attributes, such as skin color, color (whiteness) of the sclera 32, weight, posture, body-mass index, using imaging or other sensing means, as appropriate.

It is noted that baseline metrics or wellness parameter values 410 can also include temporal data that characterizes a reference feature 367. In particular, the temporally measured reference feature data relates to physiological attributes that can be expressed within the typical capture events, which are likely seconds or minutes in duration. For example, captured video data can be used to acquire temporal measured wellness parameters 410 for physiological attributes such as such as eye movements (blinks/minute, side to side motions/min.), hand tremors (mm movement/sec), gait, or other attributes that can be indicative of neurological or motor control conditions. Likewise, microphones (144) can be used to collect baseline audio data, and particularly voice data for each subject 10. The non-linguistic cues that a speaker uses to guide listeners and signal intent are collectively called prosody. Prosody includes such factors as voice pitch, pacing, and loudness and can occur consciously or unconsciously. As an example, speech analysis targeting voiced speech, which has a strong harmonic spectral structure (basically the vowels), can be a fast and efficient approach. Baseline statistical values for various temporal voice reference features 367, including frequencies, pitch, voicing rate, segment durations can be measured and then later used as wellness parameters 410 or as identifiers for subjects 10. As one approach, an auto set-up process 520 targeting voice data can include having subjects 10 read or recite vocal content that utilizes significant regions of their vocal range. Likewise an auto set-up process related to gait can include acquiring video imagery of the subjects 10 walking with a normal stride. These methods can be repeated during multiple auto set-up capture events. In addition, data from natural, rather than deliberate behavior or activities during auto set-up capture events can be acquired and used.

In summary, the auto set-up process 520 depicted in FIG. 5d nominally establishes a collection of baseline data for a system 300, as applied to one or more users 10, under a range of variable capture conditions. This baseline data includes baseline reference images 365 and reference features 367, baseline capture condition data (capture parameters 415), baseline wellness parameters 420, baseline normalization transforms, and baseline normalization confidence values. The effects of capture condition variability can be reduced by having an extended auto set-up process 520, during which sufficient data is captured under various conditions, that data variability is statistically reduced, for example by averaging. For example, relative to color normalization the whites of the eye (sclera 32) can be particularly useful. The auto set-up process 520 can establish baseline values for scleral color or whiteness, normalization transforms, and normalization correction factors. These values can be averaged, to reduce the potential impact of the eyes being bloodshot or the sclera may be segmented to eliminate contributions of the vascular system to the color of the sclera. Additionally, the users 10 can also be provided with guidelines or instructions regarding the auto set-up process 520, to direct them through a range of capture conditions. For example, these guidelines can direct users 10 through a range of poses and lighting conditions on multiple days, to aid the system in assembling robust baseline data.

To better understand the operation of physiological monitoring system 300, FIG. 5b illustrates the well-being image capture process 550 and the image normalization process 500 in greater detail. Image capture using reference image data (previously acquired during an auto set-up process 520) can then proceed as follows. For example, each day, the physiological monitoring system 300 can obtain images of each subject 10. When the physiological monitoring system 300 identifies a target subject 10 within its field of view, the well-being image capture process 500 is engaged. During this process, the system will continuously monitor the subject 10 to obtain at least one image of the subject 10 under the preferred target conditions for that particular individual. These preferred conditions are quantified by the reference images 365 and the capture parameters 415 stored in the capture parameters database 450. Camera 120 can be capturing (step 552a) one or more still images, or video images, while the subject 10 is monitored with the user tracking process 515. Camera 120 would adjust focus of the imaging lens 122 to ensure that the captured images are sharp. A stream of video images can be directed to temporary memory, and key-frame, key video extraction or video summarization can be used to identify and retain one or more images that meet the target criteria. Audio data, including voice data, for the subject 10 can also be recorded, as the opportunities arise.

The well-being image capture process 550 seeks to acquire images (step 552a) that correspond to one or more reference images 365 for a given particular individual, and satisfy the capture criteria (step 552b), expressed as the capture parameters 415, relative to variables such as image size, subject pose, motion blur, and lighting. As one example, during the well-being image capture process 550 the system (step 552b) would look to acquire one or more images of an individual in a pose that is most similar to a standard pose(s) of a reference image 365. If the pose obtained is within predetermined tolerances, and the other capture criteria are met, image data will be captured for that capture event and the system can proceed to the normalization process 400. If the pose obtained is outside the target range, the system can store the best image it obtains, and wait for an opportunity to collect a better image (that day) for a given particular individual. Ultimately, sub-par image data with an out-of-target (within some range) lighting or pose can still be used for at least some purposes.

For example, while the lighting available for a given image can be inadequate for acquiring good color images, thus preventing useful color based physiological assessments, other parameters, which do not rely upon color imaging, such as posture, gait, or eye movements, can still be assessed. Additionally, face geometry algorithms can salvage some images that are sub-par relative to pose. Such algorithms can be used to estimate the angular displacement of a face 25, and then using 3D reconstructions of the face 25, a 2D representation can be calculated that enables appropriate measures. In particular, the face geometry algorithm can use distance reference features 367, such as the calculated distance between the eyes 30 to estimate the facial orientation. This derived value can be compared to the eye-to eye distance derived from the reference images 365 for that subject. Other capture data, such as the focal length of the imaging lens 122 and the calculated distance to the subject can also be used to assess or correct for image pose or orientation, as well as help verify the eye-to-eye distance. Additionally, these 3D geometry measurements and corrections can be based on data collected from a multiplicity of image (video) frames. If the physiological monitoring system 300 has multiple capture cameras 120, including possibly with stereoscopic imaging capability, then images from a combination of cameras can be used to acquire an image within the target pose or orientation range. Stereoscopic imaging can also be used to measure the distance to the subject either with a dual lens rangefinder module or through a range map generated from a disparity map produced from the pixel offset information for a set of images captured by multiple cameras with similar fields of view. A dual lens rangefinder module is described in U.S. Pat. No. 4,606,630, which was issued to Haruki. A description of a method for producing a range map from a disparity map is described in U.S. Patent Application Publication No. 2006/0193509 published in the name Criminisi.

In large part, the target criteria for a good well-being image capture anticipate the needs of the image normalization process 400. As will be discussed, image normalization relative to color is also very important, and depends on the derivation of color calibration data. Of course, the apparent image color is very dependent on the lighting conditions. To begin with, the physiological monitoring system 300 can monitor room lighting conditions to verify that the capture is taking place under standard conditions. For example ambient light detector 140 can measure the light level in the room to determine whether the light intensity is high enough that the signal to noise levels for the image data should be acceptable. Ambient light detector 140 can also include spectral filtering or spectral dispersion devices (such as dichroic filters or diffraction gratings) to enable measurement of the optical spectrum of the ambient light 200. The spectra of the capture light 220 can also specifically be measured. Depending on the color correction criteria used, it can be sufficient for the physiological monitoring system 300 to use the spectral data simply to estimate a blackbody color temperature that approximates the room lighting. For example, typical daylight solar radiation approximates a 5900 K blackbody source. Alternately, spectral measurements can be obtained at a few choice wavelengths so that the physiological monitoring system 300 can assess the degree to which the ambient light 200 or capture light 220 includes common residential lighting spectra (such as from sun-light, incandescent lights, fluorescent lights, or LED lighting), either individually or in combination. For example, an effective light source model can be assembled by determining that the ambient light 200 at a given moment is ~25% daylight and ~75% fluorescent lighting. Finally, the ambient light detector 140 can include a monochromator or a spectro-radiometer, to obtain detailed spectral measurements. A newly captured light source spectrum or model can also be compared to prior RGB or spectral data and color correction data or normalization transforms that can be maintained and updated for capture from a given electronic imaging device 100. If a new light source is detected in the environment, the auto setup process can be reinitiated to establish baseline capture conditions that include the newly detected light source. This data can then be included as capture parameters 415 in the capture parameters database 450. In general, the different spectra available at a given location are quite variable and can change slowly (for example, seasonally) or quickly (for example by turning on or off a room light). A measured ambient light spectra or light source model can then be used to derive white point and color correction factors that can be applied to newly captured images during the image normalization process. Alternately, relative color measurements can be accomplished on the scene background to identify changes in the spectral characteristics of the lighting for the environment over a period of time.

As can be seen, various methods for measuring or deriving the intensity and spectra of the ambient and capture light are possible. The quality or accuracy of both the derived capture parameters 415 and the derived normalization transforms can depend on the measurement methods. Thus, normalization confidence values can be statistically derived, which are associated with the measurement method, the capture conditions present at a given capture event, and the type of normalization transforms For example, color correction normalization transforms can have associated color correction normalization confidence values, which can be different depending on the quality of the spectral measurement method used.

Exemplary capture parameters 415 (see Table 1) can be the intensity of the ambient light 200 in mW/cm$^2$ or in lumens, the focal length of the imaging lens 122 in mm, the distance from the camera to the subject in mm, and the spectra of the ambient light 200 of the capture light 220. The white point correction data can be expressed in various ways, including as CIELAB or tristimulus coordinates. It is noted that the color corrections and white point derived from measurements of the ambient light 200 in a room may not actually represent the light spectra falling on the subject, or a portion thereof. Physiological monitoring system 300 can use a tracking limited angle light collector device to make sure that the ambient light 200 collected for measurement is indeed reflected from a target area (such as a face) of a subject 10. The system can also measure the spectrum of the light collected by the imaging lens of camera 120. Physiological monitoring system 300 can also be provided with an illumination light source 215 that supplies illumination light 210 with an expected spectral profile.

Taken together, the well being image capture process 550 principally includes capturing (step 552a) one or more images of a subject that satisfy known conditions (step 552b) for lighting and focus, target conditions for image pose, and expected target conditions for image size (using the eye-to eye distance, for example). The newly acquired images for a given particular individual from a capture event are then certified as acceptable (step 552c), stored in memory 345, and passed to the image normalization process 500. Updates to the capture parameters database 420 can also be made during the well being image capture process 550, to record the capture parameters 415 corresponding to the new image captures. The image normalization process 500 (see FIG. 5b) is structured to derive (step 502a) and calculate normalization transforms or correction factors for image attributes such as color and size, validate the derived normalization data (step 502b), and then apply (step 502c) these transforms to the newly acquired images. Various normalization confidence values can also be calculated to indicate the quality of the captured data. The image normalization process 500 can also include calculations of updated values for some capture parameters 415, which will then be retained in the capture parameters database 420.

Size normalization of the captured images will be of importance to the well-being monitoring system. For example, the derived distance between the eyes 30 for a newly captured and certified image can be compared to the expected sizing information obtained from the reference images 365 collected during the auto-setup process 520. Corrective factors can be derived and applied to compensate for parallax errors related to the subject pose during image capture. Corrective factors can also be applied which compensate for the aberrations (such as distortion) of the imaging lens 122 of camera 120. The entirety of the new image can be scaled accordingly. Distances to various facial features, such as mouth 60, nose, ears, as well as the horizon edges of the cheeks can then be calculated.

Relative to size normalization, it can be desirable to maintain multiple size references using multiple reference features 367 related to attributes for size. For example, because of pose issues, a vertical metric or correction factor, such as the distance from the eye centerline to the centerline of the upper nostril edges can be used. The associated size normalization confidence values (used in step 502b) can help the system select which normalization transforms to apply. Likewise tracking one or more reference features 367 and the associated metrics, both horizontally and vertically, for the torso and other body regions can also useful. The use of multiple size related reference features 367 is useful not only to obtain robust size normalization given pose variability issues, but also to provide additional wellness parameters 410, which for example can enable the physiological monitoring system 300 to monitor changes such as the weight or growth of an individual unobtrusively.

Figure 6:
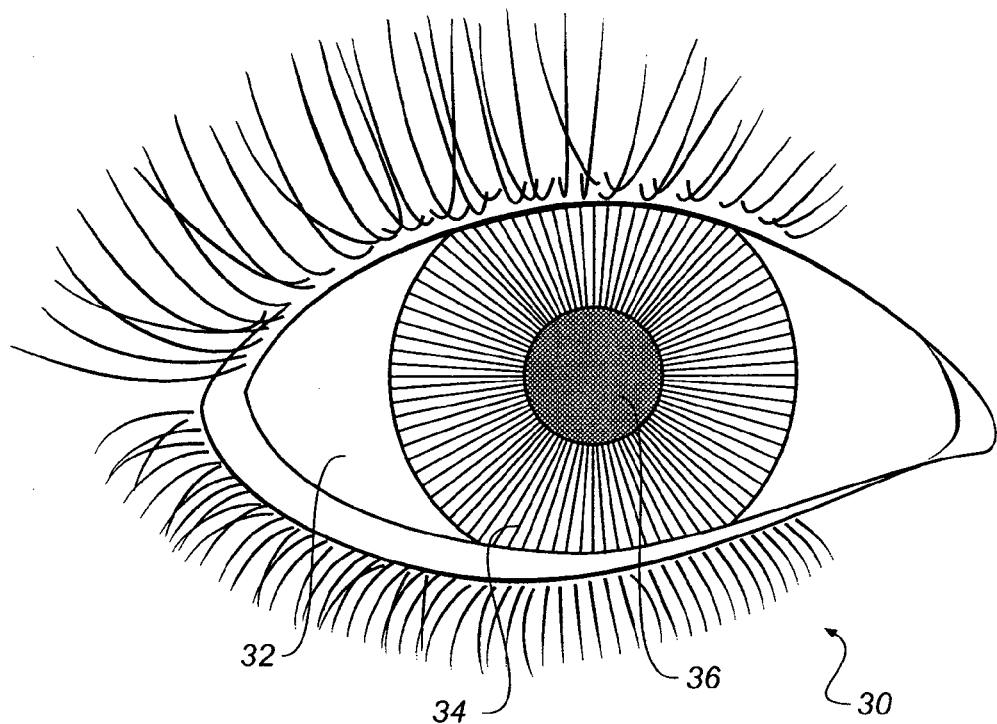
FIG. 6 is a picture of an eye, showing the sclera relative to the iris and the pupil.

The color correction or color normalization process is comparatively more difficult. As previously stated, color corrections based on spectral measurements of the ambient light 200 can be obtained (step 502a), validated (step 502b), and used (step 502c). However, there are alternate approaches for obtaining color correction data directly from the image data. That is, the color correction portion of the image normalization process 500 for the physiological monitoring system 300 can key on reference features 367 of the human body 20 that are less susceptible to external changes from factors such as sun, wind and makeup. In particular, the sclera 32 of the eye 30, shown in FIG. 6, which is more commonly known as "the whites of the eye", can be reasonably expected to be white on a repeatable basis. The sclera 32 appears to extend from the edge of the iris 34 to the edge of the eye 30, but it actually surrounds the cornea all the way back to the optic nerve. The sclera 32, which serves as a protective outer coat for the eye, is a tough, leather-like white tissue which predominately includes Type I collagen. Collagen is an elongated or rod-like molecular protein that forms in fibrils, which in turn are organized into larger collagen fibers. Although collagen has minimal light absorption, the size of the collagen fibrils and fibers is such that light in the optical spectrum is broadly scattered for all wavelengths, including the visible ones. As a result of the broad-spectrum light scattering, collagen appears white when viewed externally.

To enable this, the face recognition algorithm of physiological monitoring system 300 can use an algorithm that detects the eye 30, the iris 34, and pupil 36, within an image to help locate the sclera 32. As an example, aspects of commonly assigned U.S. Pat. No. 7,058,209, *Method And Computer Program Product For Locating Facial Features,* by Shoupu et al., can be used for this purpose. Once the sclera 32 has been located within the image, the pixel data can be extracted and color data, color correction normalization transforms, and normalization confidence values can be calculated. The detected color difference between the white point measurements for newly captured images can be compared to the white point targets derived from the data from the reference images 365 collected during the auto-setup process 520. Both white point and color corrections can then be applied to the newly acquired images so that the corrected skin tones are true.

The sclera-based white point color differences, normalization transforms, and associated confidence values can also be compared to the color corrections that can be derived from the spectral data measured from an ambient light detector 140 having a spectral measurement device. Again, both current and historical color correction data from spectral measurements can be used for comparisons. If sclera-based and spectral-based color calibrations are being used concurrently for new image captures, then the derivable color corrections for a given image capture should match, within some tolerance range, provided that the confidence values are statistically sufficient (validation step 502b). But, for example, if the derived color corrections do not match, the existence of such differences can be indicative of a physiological change in the sclera of the subject, particularly if the scleral-based color corrections show changes over time, while the spectrally derived corrections are generally constant. If comparable color changes are seen for multiple subject or family members being monitored by a system 300, then such differences can be indicative of a system error or a macro-environmental change. As can then be anticipated, it can be useful to maintain and track both normalization transform and confidence value data over time.

Although color or whiteness of the sclera 32 is a good color correction reference point, there are other potential color reference features 367 related to other anatomic attributes for color. For example, other body features, such as the tongue or teeth, which are less prone to color changes from external factors than is the skin 40, can also be used for deriving color calibration data. Admittedly, teeth coloration is very dependent on the quality of dental care and can vary somewhat in response to foods or beverages that have been consumed prior to image capture. Alternately, color components of skin tone that tend to be common to all ethnic groups, regardless of their apparent skin color, can be measured and used. Given that such features can be considered invariant relative to color, they can be used to calculate color normalization parameters for imagery captured under the various standard lighting conditions (light level and color temperature). Taken together, spectral measurements, scleral "whiteness" measurements, tongue color measurements, or other such measurements can be used in combination to reduce the risk of errors in color calibration. Nominally, the color normalization for a given capture event will use the available color correction transform data having the highest confidence values. However, the highest values may be too low for accurate color normalization of all the color data, but can still be sufficient for some color-related physical attributes. Under such circumstances, the normalized data can be tagged to indicate the quality of the normalization. As another point, if all the color related physical attributes being tracked for a given subject do not require particularly accurate normalization methods, an easier, but sufficient method could be the regular method of choice.

It is noted that neutral or color reflectance standards can be provided with the system 300, to enable validation of the color correction. However, as these reflectance standards can be lost, marred, or otherwise inconvenience the user, such an approach is not preferred, and may be best suited for the auto set-up process 520. In any case, white point and color correction terms can be derived by various methods, and then retained as additional capture parameters 415 that are retained in the capture parameters database 420.

Following the operational process of physiological monitoring system 300 diagrammed in FIGS. 5a and 5b, the well-being image capture process 550 results in one or more newly acquired images being certified (step 552c) relative to factors such as size, pose and lighting. Once the image normalization process 500 has obtained color correction data, size correction data, and other correction data (step 502a), these data can be validated (step 502b) and applied (step 502c) to correct or normalize the newly acquired image of an identified subject. In many cases these changes are advantageously applied on a pixel-by-pixel basis. Corrections for color, size, and resolution errors caused by the imaging lens 122 can also be applied as necessary. As a potential further step, then newly captured and normalized images can be transformed from 2D image views to 3D image views using an appropriate algorithm. In some cases, well-being analysis and assessments, as well as image presentation, can be improved by working with 3D imagery.

Although the image normalization process 500 has been specifically described as an image-based process that is focused on color and size issues, normalization has broader purposes in the present invention. For example, temporal data related to physiological attributes such as gait or eye movements or hand movements can be extracted from the video image data, normalized for current capture conditions, and retained to support assessments of mechanical or neurological conditions. Likewise, the system 300 can include microphones (a type of secondary detector 144) and an audio processor within computer 340. Audio data, and particularly voice data can be collected during a capture event, and the resulting data can be normalized in intensity or frequency space to enable subsequent derivations of wellness parameters 410 and wellness assessments.

The image normalization process 500 is typically followed by the calculation of wellness parameters 410, which can be undertaken by a computer 340, either as an intermediate step prior to the operation of the inference engine 400, or as a first process of the inference engine 400. As shown in Table 1, the semantics database 430 can contain data that a given subject has known or suspected physiological conditions, such as Alzheimer's or anorexia. The wellness parameters database 420 can then utilize both general and condition associated wellness parameters 410 appropriate for tracking the physiological conditions within the capabilities of the system 300. The wellness parameters 410, such as the examples listed in Table 1, are effectively the bookkeeping means for quantitatively tracking physiological conditions, supported by ongoing calculations of wellness parameter values with succeeding capture events. New values for the wellness parameters 410 can be directly calculated from the collected and normalized image (or audio or other) data. The wellness parameters can also be derived by more complex means, using data from combined data sources or complex mathematics. In some cases, given wellness parameters may not be accurately known, or may be known to change with known ranges. This uncertainty can be expressed with ranged values, error bars, or with wellness parameter confidence values.

As one example of calculating wellness parameters 410, a color corrected image can be analyzed spatially to look for both localized and macro regions of common or related colors. In particular, one standard wellness parameter 410 can be the average color of the skin 40 of the individual's face 25, or within one or more areas of the face 25. A further wellness parameter 410 can be a slope of the average skin color for an area over a period of time, as a means of looking for trend-line type changes. It is expected that system 300 will have a set of both standard and individualized wellness parameters 410 that it checks for each subject. Other facial standard wellness parameters can include the skin color below the eyes, the location of hairline, or the facial width across the horizon lines of the cheeks. Standard wellness parameters 410 can also be derived for other parameters such as weight and posture, relative tiredness, emotional state, personal care or hygiene, or dental care, depending on the image capture and algorithms being used. As an example, personal care can be tracked with a wellness parameter that combined measures of hair care (length, neatness), dental care (cleanliness, tooth brushing activity), skin care (cleanliness), and clothing state (neatness, quality). Other standard wellness parameters 410 can relate to tracking longitudinal changes in any of the wellness parameters 410. Some wellness parameters 410 can be tags to identify known or suspected user conditions, such as tracking or identifying that a given subject 10 has diabetes or Alzheimer's. Additionally, customized or individualized wellness parameters 410 might include tracking localized color changes related to acne, rashes, or wounds (acute or chronic). Other customized wellness parameters 410 can relate to known familial genetic conditions or historical tendencies, as well as monitoring for proper use of some medications. Wellness monitoring, and the accompanying wellness parameters 410 can also be provided for tracking the effect of skin treatments and cosmetics on the color, texture, moisture levels, or sub-surface structure of skin.

Thus wellness parameters 410 can be values quantifying direct physical attributes, or they can be derived values, such as averages, slopes, trend-line or abrupt threshold values, longitudinal change metrics, frequencies, and other combined values. Derived wellness parameters can also include error bars or wellness parameter confidence values. Thus wellness parameters 410 will take various forms, depending on the physiological conditions being monitored or the calculations used. For example, body weight data can be calculated and retained as number in lb or kg units. Skin color, for example, can be calculated and retained as numbers in units of hue angle and color saturation. The color of the sclera 32 can be calculated and retained as a correlated color temperature value or in terms of CIELAB color coordinate space values or values of other commonly used colorimetric spaces. As another example, skin texture can be tracked using measures for the surface roughness, roughness orientation, and elevation of the skin compared to the surrounding skin. Standing posture can be tracked relative to the curvatures of stooped or slumped shoulders and the curvature of the small of the back.

Accordingly the physiological monitoring system 300 is maintaining and tracking capture parameters 415, semantics data, normalization data, and wellness parameters 410 in the respective databases. This historical data can be retrieved and used for the calculation of updated wellness parameters and trend-lines thereof (for capture parameters and wellness parameters). The physiological monitoring system 300 can then update (see FIG. 5b) the wellness parameters database 420 with the newly calculated wellness parameter data (410), including updates to any ongoing trend-line tracking. In one context, many of the wellness parameters 410 can be considered to be a specialized type of image metadata that are specifically related to health and well-being. Although many wellness parameters 410 are linked to associated reference images 365, these data are not likely stored as metadata in the image file structure, as a database structure will better facilitate the data access required for the various calculation and comparison processes internal to physiological monitoring system 300.

Once wellness parameter calculations are completed from data acquired for a particular individual during a capture event, individual wellness can then be assessed using the inference engine 400 (see FIG. 5c), which is a specialized program or algorithmic structure (implemented in software or hardware) that looks for potential physiological changes. In particular, it can examine (step 402a) the ensemble of wellness parameters 410 both individually and in combinations, to look for physiological trends or changes. It can compare (step 402a) any newly derived wellness parameters 410 to both the wellness parameters 410 derived from the reference data, and to the longitudinal record for the wellness parameters 410, including the trend-line type wellness parameters 410. The inference engine 400 can also compare the newly captured image data to the data of the reference image 365 and the longitudinal record of images (and reference images 365) for that individual. In effect, the inference engine 400 is determining whether statistically significant changes in the wellness parameters 410 can be associated with physiologically significant changes. The image and health data assessment process conducted by the inference engine 400 is intended to watch for both subtle and dramatic changes that can be indicative of physiological issues related to an individual's well-being. The inference engine 400 can analyze (step 402a) whether current wellness parameters 410 are stable or trending in a known direction, for example monitoring the slope, direction, and locations of a color change over time. The inference engine 400 can employ a threshold or step function change criteria to identify a trigger (step 402a); that is a tag that a notable physiological change may have occurred. While thresholds, triggers, and action limits are specified and acted on by the inference engine 400, they can be expressed in terms of wellness parameters 410 that the physiological monitoring system 300 can calculate and monitor on an ongoing basis. Again, wellness parameters 410 can be used for multiple uses. For example, a skin dryness wellness parameter 410 can be compared to metrics for cosmetic reasons or for health reasons, such as related to the potential formation of wounds, and thus different test action limits may apply.

The inference engine 400 can also compare (step 402a) wellness parameter data 410 of one individual to that of another, to look, for example, for a trend in physiological changes that might be common to several family members. If the inference engine 400 does not identify any significant changes in the wellness parameters data 410, including the trend line data, that is associated with a set of newly acquired images, then the inferring efforts can stop for that capture event.

When the inference engine 400 identifies potentially significant changes according to its known standards for the wellness parameters 410 it tracks, a series of validation and assessment activities ensue. As one aspect, the ongoing changes, following either a trend line or trigger, can be assessed via a health database 460 that documents a range of known health and medical conditions. Such a database can be stored and maintained locally with the physiological monitoring system 300. Additionally, an externally updated database can be accessible via a network (such as a mobile communications network or the Internet), which the physiological monitoring system 300 can access via network 360. Access can occur automatically on an as-needed basis (the system has detected a change but lacks clarifying data), or by a schedule, or by direction of a user 10. The inference engine 400 can then access these wellness or health databases 460, and look for data regarding the potential significance of changes related to the identified trends and triggers. The inference engine can initiate a new wellness parameter 410, which can be back calculated if the data is available, that is more applicable to a new concern than were the pre-existing wellness parameters 410. Likewise, as new medical or health related knowledge becomes available, the physiological monitoring system 300 can be updated to add new wellness parameters 410 to the list being tracked, or to apply the pre-existing data towards screening for a new concern. After collecting relevant data from the health database 460, the semantics database 430, and the capture parameters database 450, inference engine 400 can test (step 402b) the trend lines or trigger data to see if they still appear significant.

Additionally, the inference engine 400 can use a process for testing for false positives in its assessments of physiological conditions (step 402c of FIG. 5c). A variety of system data, including semantic data, wellness parameter data, capture condition data, normalization data; can be utilized as part of false positive testing. As an example, false positive testing can access the semantic database 430 that maintains data regarding factors (see Table 1) such as subject age, travel schedule, exercise patterns, medication usage, or the use of cosmetics, that can effect skin color and other physiological factors or conditions. Thus, as shown in FIG. 5c, if the inference engine 400 detects an apparent physiological change, it can access the semantic database 460 and look for potential causes of a false positive. Semantic understanding can also provide data regarding time of day and year that can be indicative of lighting conditions and changes. Of course, the semantic database 460 may not be aware of events or activities that may have caused a potential physiological change. For example, the semantic database 460 may be unawares of a vacation trip to the Caribbean, or the use of a tanning bed, that results in a "sudden" skin color change that is subsequently detected by the physiological monitoring system 300. Inference engine 400 can infer that a particular type of color change may be a result of tanning and then flag the physiological monitoring system 300 to watch to see if the tan fades over time. Alternately, the physiological monitoring system 300 can query a local user concerning the significance of the observed change.

As another example, the inference engine 400 can access the capture parameters database 450 and the normalization data as part of the false positive testing process (step 402c). In particular, apparent changes that are due to variations in capture conditions rather than wellness changes should be identified to reduce false positives. As examples, color changes or size changes can be attributable to either differences in capture conditions or changes in physical attributes. Thus to enable robust testing for false positives, the system 300 preferably maintains and tracks multiple color capture parameters 415 and color correction factors (such as from the sclera, skin, or measured spectrum) and multiple size based capture parameters 410 and size correction factors (such as eye-to-eye, or eye to nose). The previously mentioned normalization confidence values can play a key role here, as the inference engine can examine both current and prior normalization transform values and associated normalization confidence values to ascertain whether changes in the capture conditions or system performance may be effecting the calculated wellness parameters 410 or wellness inferences. For example, the inference engine 400 can determine, with high confidence (high probability) that a normalization transform has shifted significantly from nominal. Alternately, the confidence values associated with a given normalization transform can be deemed low enough that any resulting inferences are suspect. Recognized uncertainty in the wellness parameters 410 can also be factored in. It is noted that capture condition variations, whether abrupt or trend line changes, can be expressed in either the capture parameters 410 or the normalization transforms. At times a user 10 will need to be alerted to changes in the physiological monitoring system 300, ambient conditions, or other factors that are affecting the functional performance of the system. Inferences concerning physiological conditions can also be reported to users with commentary concerning the confidence level of the inferred conclusions.

The physiological assessment steps and the validations steps (402*b* and 402*c*, using semantic, capture, wellness, and normalization data) can be conducted sequentially, iteratively, and in various orders. In this way, imagery can be monitored for changes in skin color or hair appearance that might indicate a change in one or more physiological conditions. For example, bluish skin hue can be indicative of eating disorders or side effects from drugs. As another example, any trends in the color correction normalization parameters that might suggest a gradual change in the color of the eyes 30 or sclera 32 can be evaluated to determine if an underlying condition that manifests itself in eye color has been detected. Of course, these assessment and validation steps can also be applied to non-image-based data collected by the system 300.

If the inference engine 400 concludes a capture data assessment process with a determination that it has potentially detected a meaningful trend or change for a given particular individual, then physiological monitoring system 300 can notify a local or remote user 10, a clinician, or other party. Most simply, the system can provide a local alert 350, using an audio or visual cue, for example provided through a display 110 that is built into an electronic image device 100. Physiological monitoring system 300 can also send an e-mail alert to one or more pre-determined e-mail addresses. Alerts and reports can be provided with varying degrees of urgency, ranging from "please take vitamins" or "please get less sun exposure" to harder recommendations, such as "please discuss with your physician next time you see them" to "please see your physician now". As another option, a user 10 can be asked to position themselves in front of a system camera 120, so that additional images can be obtained.

Additionally, if relevant, a standard medical data format, such as for an electronic patient record, can be used. For privacy reasons, the detailed reports may only be accessible by any designated lead users, such as "Mom". A display 100 can subsequently show image data and wellness parameters 410 illustrative of the potential concern. Physiological monitoring system 300 can also provide a compiled report which can include a set of relevant images and image data, accompanied by one or more tables of wellness parameter data, or one or more graphs of wellness parameters 410 showing trend lines or abrupt changes, and commentary on the potential meaning or significance of the data. However, as the hard data may be difficult for many users 10 to absorb, the system can also provide a visual journal 370. Also, in some cases, the observed physiological changes can be significant, yet subtle. Therefore, this visual journal 370 can provide an image sequence that illustrates the observed changes over a relevant period of time. The visual journal 370 can employ image animation or morphing to aid visualization of the changes. The animation or morph can be derived either by changes in the shape of the face (such as caused by weight loss or weight gain) deforming the underlying mesh model, or changes in face color or texture or other characteristic shown as changes to the skin mapped over the underlying mesh. The animation or morph can be used to condense changes that occurred subtly over long periods and show them visually in a few moments. As another assist, a report or visual journal 370 can depict physiological changes with unique color change images that use boundary outlining, exaggerated color, or false color to highlight the observed changes. The visual journal 370 can be supplied as an electronic document that can be printed locally. A family caregiver, parent or physician can use (step 402*d*) the visual journal 370 or other report to determine when a symptom or change manifested itself, and how the physiologic condition changed over time or with medical intervention.

As noted previously, personal and family privacy management is a key aspect of the physiological monitoring system 300. Table 1 summarizes a range of privacy settings that can exist within the privacy settings database 440. The privacy issue interacts with the image capture process, the data management process within physiological monitoring system 300, and the data reporting process. To begin with, in considering the range of variation in people's height, particularly from children to adults, it is likely that the original image capture will span a wider field of view than will be generally needed. A given electronic imaging device 100 can be equipped with multiple cameras 120, having for example, both lower and higher positioning. The cameras 120 will probably be oriented to capture a wide field of view image in portrait mode. Additionally, these cameras 120 can also have pan, tilt, and zoom controls. Thus, it is likely that images captured during the well being image capture process 550 will capture body imagery of much more than just the face 25.

Privacy is a complex issue, which involves personal preferences, family dynamics, legal boundaries, along with societal, cultural, and religious expectations. In the case of physiological monitoring system 300, these privacy issues interact with legitimate health and medical concerns. As one example, while there are legitimate reasons to image family members (the subjects 10) using this system, and while this system is typically used to image family members and not visitors, other steps can be taken relative to visitors. For example, when the system identifies an individual as a non-subject of interest, it can, in addition to not retaining any image data, issue an alert so the non-subject individual knows the system is present. As another option, the local users 10 can shut the physiological monitoring system 300 down for a length of time in advance of an event, such as the hosting of a party.

Considering again the likelihood of an initial wide field image capture by cameras 120, an individual user 10 may be uneasy about having the physiological monitoring system 300 regularly capture and store torso or full body images, even though the physiological monitoring system 300 is installed in their residence and under their control. As such, the default condition for physiological monitoring system 300 is for it to only save the captured wide field of view images cropped down to just head and shoulders images, as with the reference image 365 depicted in FIG. 7. Likewise, an alternate default condition can be for the physiological monitoring system 300 to tabulate and retain wellness parameter data 410 calculated only from these facial images. However, an individual user 10 can have legitimate reasons to want to collect image based physiological data of themselves or another family member that can include torso or full body data. It is likely then that different degrees of privacy management will be available, and can even be applied differently for different family members. As a result, a privacy settings database 440 is anticipated, including a set of subject specific privacy setting parameters (see Table 1).

For example, as an intermediate setting to collecting and maintaining a collection of torso or full body images over time, the physiological monitoring system 300 can collect and retain facial imagery in combination with wellness parameter data 410 for both the face 25 and torso 50. As another intermediate setting, the physiological monitoring system 300 can collect and maintain torso or full body imagery, along with the associated wellness parameters 410, but with the image data for the generally private body areas respectively blurred or cropped out. Certainly, access to the physiological data, and particularly the image data, will likely be quite limited in order to maintain confidentiality. Both password protections and data encryption can be used for this purpose. Other identification based access control technologies, such as voice, fingerprint, gesture, or other biometric approaches can be used, either individually or in combination. For example, in the family setting, only the parents are likely designated as the "lead users", who then have direct and privileged access to the data and the system controls.

In general, the privacy settings managed by the privacy setting database 440 include a list of subjects 10, data regarding identifying attributes to recognize the subjects 10, and access controls associated with the subjects 10. The privacy settings further include control information on how to capture, process, store, alert, report, and share the data produced by the system 300. These various privacy settings and linked identity information can be accessed via a privacy interface, such as a graphical user interface, that can be accessed by a user 10 (a lead user). These privacy settings nominally apply to image data and image-based data, but also to non-image data (such as audio). The privacy settings can be applied in various ways to control and enable the sharing of the data with medical professionals. Obviously, the physiological monitoring system 300 is intended to work in an environment where the local individuals (the users 10) generally desire its features and capabilities. As such, the physiological monitoring system 300 must provide a useful balance between providing value, while maintaining privacy and reducing any imposed burdens unnecessarily.

It is also recognized that circumstances will occur where a user 10 intends to use the physiological monitoring system 300 to deliberately collect physiological image and wellness data, facial or otherwise, over a period of time. For example, a user 10 may want the teeth or gums of a family member to be imaged on an ongoing basis. Likewise, image and wellness data may be wanted with respect to a rash or a slowly changing chronic wound. In such instances, the user 10 will need user access at an electronic imaging device 100 to instruct it to deliberately capture and retain the image data, even if the images include privacy sensitive areas.

It can be anticipated that the both the semantics database 430 and the wellness parameters database 420 would include data that is directly entered by users 10 (likely by a lead user). For example, users 10 can provide the semantic data relating to known familial genetic conditions or historical tendencies, as well as medications being taken, acute conditions of concern, or other factors. A user 10 can alert or tag the system with current wellness data (for example, that a family member does not feel well, is sick, has the measles, or is depressed) that the system might not otherwise have knowledge of. Likewise, a user 10 can provide input to the system regarding the user's own inferences or conclusions concerning the wellness of a family member, whether drawn from the output data provided by the system, or from other sources. Generally, the system 300 would then provide appropriate wellness parameters 410 associated with this information. Additionally, either the system 300 or the users 10 can provide customized wellness parameters 410 specific to one or more subjects. Any data for user entered wellness parameters 410 can be managed within a subset portion of the wellness parameters database 420. A user's inferences or conclusions can also be input into the inference engine 400, with a request that it test their potential validity. The dashed lines of FIG. 5c indicate the potential for outside (such as from users 10) inputs and requests to the operational flow of the system.

In a broader context then, the definition of unobtrusive for physiological monitoring system 300 is somewhat malleable. In general, on an ongoing daily (weekly or monthly) basis, the system is intended to operate inconspicuously, with little attention or care required. Some users 10 can be more comfortable with the physiological monitoring system 300 if it provides a modest alert, such as a flashing light or an audio tone, when it is about to proceed with a well-being image capture. Other users 10 may prefer to deliberately direct the system to capture an image, and then deliberately pose for the capture event. Of course, when the physiological monitoring system 300 detects a potential issue, which may reflect a gradual or abrupt physiological change, it is supposed to provide one or more alerts, which can be communicated differently depending on the circumstances. For example, an electronic imaging device 100 can provide an alert locally, via a display 110 (with an icon, for example) or a flashing light, an audio tone, but the detailed data may only be accessible at another location (to a lead user) on the network 360. Also, various settings regarding privacy, access, and reporting can be user controlled either locally at the electronic imaging device 100 or by a user interface program run through a computer located within the residence.

In that context it should be understood that the computer 340 which interfaces with memory 345, cameras 120, display 110, controller 33, and image processor 320 can be a specialized device intended for this purpose, and thus can be separate from any home computer found in a residence. Such a computer could be part of the imaging device associated with the system or associated with another multi-functional device owned by the user (examples might include a mobile device such as a smart phone or a gaming console). Computer 340 can have its own display and keyboard for direct usage. Alternately computer 340 can be connected via a network 360 with another computer located in a residence. Computer 340 can also be an existing computer within a residence, or a combination of computers, both within and outside a residence. Likewise memory 345 can include one or more devices, using one or more data storage technologies, and exist both locally and remotely (off premises).

It is recognized that physiological monitoring system 300, which is primarily intended for use in the residential environment, must readily adapt to a wide range of conditions and situations. The ambient lighting can change quickly over a wide range of conditions. The users can change the privacy settings, or turn the system off for some duration (such as for a party). As another dynamic, it can be anticipated that occasions will occur where the system detects multiple individuals within its field of view. As one simple default response, the system can suspend image capture activities until there is only one potential subject within its field of view. Alternately, the system can analyze the initial imagery with the subject identification process 510 and determine if any of the individuals present are known target subjects. If so, the well-being image capture process 550 can then proceed. Thus it is recognized that both the subject identification process 500 and the well-being image capture process 550 will need to be capable of processing image data for multiple individuals (users 10) simultaneously.

On another point, physiological monitoring system 300 can revisit the auto-set-up process 520 over the course of time. For example, as a person ages, particularly during youth, adolescence, or the elderly years, dramatic physical changes are typical to the human experience. For example, as adolescents mature, dramatic changes in height and facial features often occur. Thus while the original reference data (such as a reference image 365) collected at some earlier time likely still have value, the system 300 will require new baseline data to increase its utility. Thus, based on an automatic assessment criteria or user input, the physiological monitoring system 300 can undertake a secondary set-up process to establish new baseline data. Most simply, this likely means that over a suitable period of time the physiological monitoring system 300 will collect and process extra data to use in assembling a new reference data set. For example, inference engine 400 can be used to conclude that new baseline data is needed. Inference engine 400 can apply knowledge of factors such as the age of subjects 10, taken from the semantics database 430 or the wellness parameters database 420, as input to such a decision. A user 10 can also initiate a secondary auto-setup process 520 and provide supporting data.

The physiological image-based data capture has generally been described as occurring on a daily basis. It is noted that the physiological monitoring system 300 could become quickly become burdened with large amounts of data. Thus more generally, the physiological monitoring system 300 can collect data on a less frequent basis, for example, once a week, or bi-weekly, monthly, or even quarterly. For example, the system can look to capture an image daily, and then compare the results to both the reference data and recent data. If the system does not detect any significant changes, it can retain only wellness parameters 410, or the trend line data, or perhaps no data at all. Alternately, if the physiological monitoring system 300 detects a change, it can change the target rate of data measurement and retention for the relevant parameters, for example, from bi-weekly to daily. Additionally, a user 10 can change the data capture and retention rate for one or more family members.

The physiological monitoring system 300 of the present invention has been generally discussed with respect to the system being used to monitor a range of wellness conditions, such as nutrition, weight, or posture. As shown in Table 2, there is a wide range of wellness, health, and medical conditions that can potentially be monitored using this system, using one or more wellness parameters 410 (see Table 1). Of course, as many physiological changes can be attributed to more than one potential cause, the problem of false or misdirected positive results is not insignificant. Although the inference engine 400 can access health or medical databases 460 in order to screen data and provide informative alerts, physiological monitoring system 300 is best considered to be a diagnostic aid. Considering Table 2, skin color changes and localized or mottled skin color changes can be detected if camera 120 has color specific detection devices. For example, cameras 120 can have an image sensor array 124 (commonly a CCD or CMOS) including sensing pixels overlaid with a patterned color filter array (often RGB). To some extent, the native resolution of the camera 120 will impact the ability to image some of the conditions on Table 2. Simply equipping a camera 120 with a zoom lens will enhance the localized resolution and enable better imaging of the sclera 32, or skin 40 or skin texture, and other features.

TABLE 2

Examples of Visual Markers and Associated Physiological Conditions

| | |
|---|---|
| Skin color | Blue: Lack of oxygen supply in the blood caused by poor circulation, eating disorder, drug side effects |
| | Paleness: Anemia, leukemia, heart conditions |
| | Yellow: blood diseases or jaundice (whites of the eyes turn yellow as well) |
| | Flushing/redness: Stress, anxiety, guilt, exercise, rosacea, heart conditions, exposure to heat and cold |
| Mottled skin | exposure to heat and cold, rheumatoid arthritis, dermatitis (skin infection) |
| | early changes for some systemic diseases, such as meningitis and encephalitis |
| Localized area skin discolorations | Rashes - Allergies, diabetes, osteoarthritis |
| | Skin infections - cellulites, endocarditis, dermatitis |
| Bags under eyes | Lack of sleep, sinus infection, large intestine (colon) problem, or kidney problems |
| Skin texture | Localized bumps or lesions - rashes and dermatitis, skin infections (impetigo, dermatitis), tuberculosis |
| | Response to skin treatments and cosmetics |
| | Other (oily, leathery, shiny): many other conditions |
| Skin moisture level | Dry: dehydration, dermatitis, vitamin deficiencies, thyroid disorders, anorexia |
| | Moist: Acne and the treatment thereof; |
| | General: skin assessment for application of cosmetics and moisturizers, oiliness, pH |
| Hair loss | Iron deficiency anemia, thyroid disorders, eczema, lupus, chemotherapy |
| Eyes | Bloodshot: fatigue, eyestrain, allergies, infection |
| | Eye movement: nystagmus, Parkinson's disease |
| | Dry eyes: rheumatoid arthritis, rosacea, common cold |
| | Changes in sclera color: Osteogenesis Imperfecta, Pyknodysostosis, Marfan Syndrome, and others |
| Nose bleed | hypertension |
| Gums - oral health | Color changes or ulcers: diabetes, cardiovascular diseases, HIV Aids, oral infections, anemia, allergic reactions, Crohn's disease |
| Teeth - oral health | Cleanliness - dental care |
| Tongue (color, texture, and size) | Anemia, early cancer detection, and other conditions |
| Bulging neck veins | heart disorders |
| Involuntary movements | neurological conditions, hand tremors, response to drugs |
| Personal care | memory loss, alcoholism, depression, monitoring medical adherence (testing or use of drugs) |
| Gestalt | depression, Alzheimers, tiredness, nourishment, weight gain or loss, posture, gait |

However, the imaging of skin texture and structure can be significantly enhanced if polarization photography is used. According to the paper "*Polarized Light Examination and Photography of the Skin*", by R. R. Anderson, in the Archives of Dermatology, Vol. 127, pp. 1000-1005, 1991, the use of polarized illumination light combined with a polarization analyzer located prior to the detector, can improve skin imaging. In particular, if skin is illuminated with light polarized by a linear polarizer, and the polarization analyzer is aligned with an orientation parallel to the polarizer, imaging of the skin surface is enhanced. Whereas, if the two polarizers are crossed or orthogonal to each other, skin surface imaging is suppressed and imaging of sub-surface skin structures is emphasized. As skin texture is principally about surface qualities, but also depends upon sub-surface structures, both polarization-imaging modes can be useful here. Polarization sensitive imaging can also help with imaging the skin moisture level. In the case of physiological imaging system 300, this can mean that an electronic imaging device 100 is equipped with a polarized illumination light source 215 for illuminating a user. It is noted that providing electronic imaging device 100 with an illumination light source 215 having a known spectrum can also help improve the color correction and normalization process, as there may be less spectral variation to accommodate. Although providing such an illumination light source 215 can be more obtrusive under some circumstances than using the existing room lighting or daylight, it is also not unusual for a bathroom medicine cabinet or vanity to be equipped with additional lighting.

The electronic imaging device 100, including cameras 120, can be equipped in other ways to improve and expand the health imaging capabilities. For example, one or more cameras 120 can have non-visible infrared or UV imaging (wherein infrared imaging is done above about 700 nm and UV imaging is done below about 400 nm) or multi-spectral imaging capabilities, which can assist in imaging non-visible changes in the skin, hair, eyes, mouth, saliva, sweat, tears and sub-surface changes in skin structure, skin temperature and skin temperature distributions. More generally, the physiological monitoring system can image light from the EM spectrum, nominally in the spectral range from 350-2000 nm or higher. Other conditions which are reflected in involuntary movements, for example of the eyes 30 or head, might be detected if the physiological monitoring system 300 captured video images and used motion detection algorithms to quantify the motion. As another example, the inference engine 400 can use algorithms to assess an individual's gestalt (overall health) or emotional state by identifying and tracking patterns of facial expressions or personal care (grooming and appearance). In particular, facial recognition algorithms can be extended to identify an individual's emotional state by quantifying a variety of facial expressions including but not limited to mouth shape patterns (for smiles and frowns).

On another note, relative to the previously described image capture and normalization process, imaging of the sclera 32, and deriving the color thereof, was described as an approach for color correction which is applicable to the present invention. Image normalization based on scleral imaging is particularly attractive because of the simplicity and general repeatability. However, the scleral whiteness or color can change, particularly in a temporary way, when the eyes become "bloodshot" or reddened. Less commonly, some medications, such as steroids, or anemia or aging can cause the sclera 32 to thin and take on a blue tint. There are also various rare medical conditions, such as Marfan's syndrome, which can cause scleral color changes. For such reasons, it is desirable for the physiological monitoring system 300 to at least occasionally utilize other white-point and color measurement and normalization techniques. By tracking the pre-normalized scleral color (as a wellness parameter 410), capture conditions, normalization transforms and the associated normalization confidence values the system can determine if the color of sclera has actually changed over time. Alternatively a normalized secondary reference feature color can be evaluated to determine if it is within expected ranges. If not it can be inferred that the color of the sclera has changed.

In general, the discussion of physiological imaging system 300 has focused on obtaining and analyzing direct front view images of the face 25, and maybe the torso 50, of one or more subjects. However, side views images, particularly of the torso 50 are useful as well, particularly relative to assessing body weight and posture. These algorithms can access the semantic database 430, as well as the wellness and health databases 460 to utilize body type data and health quality data to provide an assessment. Also, an illumination light source 215 can employ structured lighting, to project a pattern of horizontal or vertical bars of illumination light 210 onto a subject 10 to assist the process of estimating weight, posture, and gait. This illumination light 210 can include light from the infrared spectrum (for example, 830 nm light, which humans cannot see) to maintain the unobtrusiveness relative to subjects 10.

It should also be understood that the physiological imaging system 300 can accept other data inputs for assessing physiological conditions, besides cameras 120. For example, the system can be equipped with secondary detectors 144 or connections (wireless or physical wires) to other bio-monitoring devices, such as microphones, thermometers, digital scales, sensing textiles, ear bud sensors, pulse oximeters, and saliva testing devices. One new technology, an electric potential probe, which is described in application U.S. Patent Application Publication No. 2006/0058694 by Clark et al., is particularly attractive as a secondary detector 144, as it is another non-contact device (like cameras and microphones) that can enable a broad range of physiological measurements. This emerging technology is further described in *Electric potential probes—new directions in the remote sensing of the human body*, by C. J. Harland et al., and published in Meas. Sci. Technol. 13 (2002) 163-169. Using various secondary detector devices, wellness parameters 410 such as blood pressure and heart rate, blood oxygenation, blood glucose levels, or body temperature, can be measured, and then the data can be collected, maintained, and tracked within the wellness parameters database 420. Thus its should be understood that system 300 can support the sensing and analysis of a wide range of biophysical, biochemical, or emotional markers. Accordingly, while the image normalization process 500 and the inference engine 400 have been described principally with respect to their handling of image-based data, they can be extended to utilize various types of non-image based data, including particularly voice data.

Although the physiological monitoring system 300 has been described, relative to FIG. 3, as a networked system, the system had been predominately described as including an electronic imaging device 100 built into a bathroom vanity. Application in that environment can impose particular limitations. For example, the ability of the electronic imaging device 100 to capture images can be impaired if the mirror 136 is fogged by condensation as might occur when an individual takes a shower. Of course, the outer, mirrored surface can be heated or coated to reduce this problem. It is also recognized that in many bathrooms, medicine cabinets are provided behind the mirror. Certainly, it can be expected that any cameras 120, displays 100, or other detectors or sensors (136, 142, 144) will be competing for at least some of this potential space. Again considering FIG. 3, electronic imaging devices 100 for physiological monitoring system 300 can be positioned elsewhere within a residence, including behind pictures or bedroom vanities. As another example, one or more cameras 120 can be positioned at a computer or a television, much like how web-cameras are used today. In such cases, the physiological monitoring system 300 can observe other factors than the wellness parameters 410 previously described. For example, the physiological monitoring system 300 can observe the posture, ergonomics, emotional response, attention span, time spent, and fatigue of a subject 10 at a computer or television (see FIG. 1). Such data can be useful in assessing mental stress levels, potential repetitive stress disorders such as carpal tunnel syndrome, or mental attention to a task. In the case of children, assessments of mental attention can be useful relative to conditions like attention deficit disorder (ADD) or for understanding educational performance. Additionally, the physiological monitoring system 300 can also accept inputs from other biomedical devices, including hand held or wearable sensors. These supplemental devices can also include PDA or cell phone type devices that have imaging capabilities.

Figure 2B:
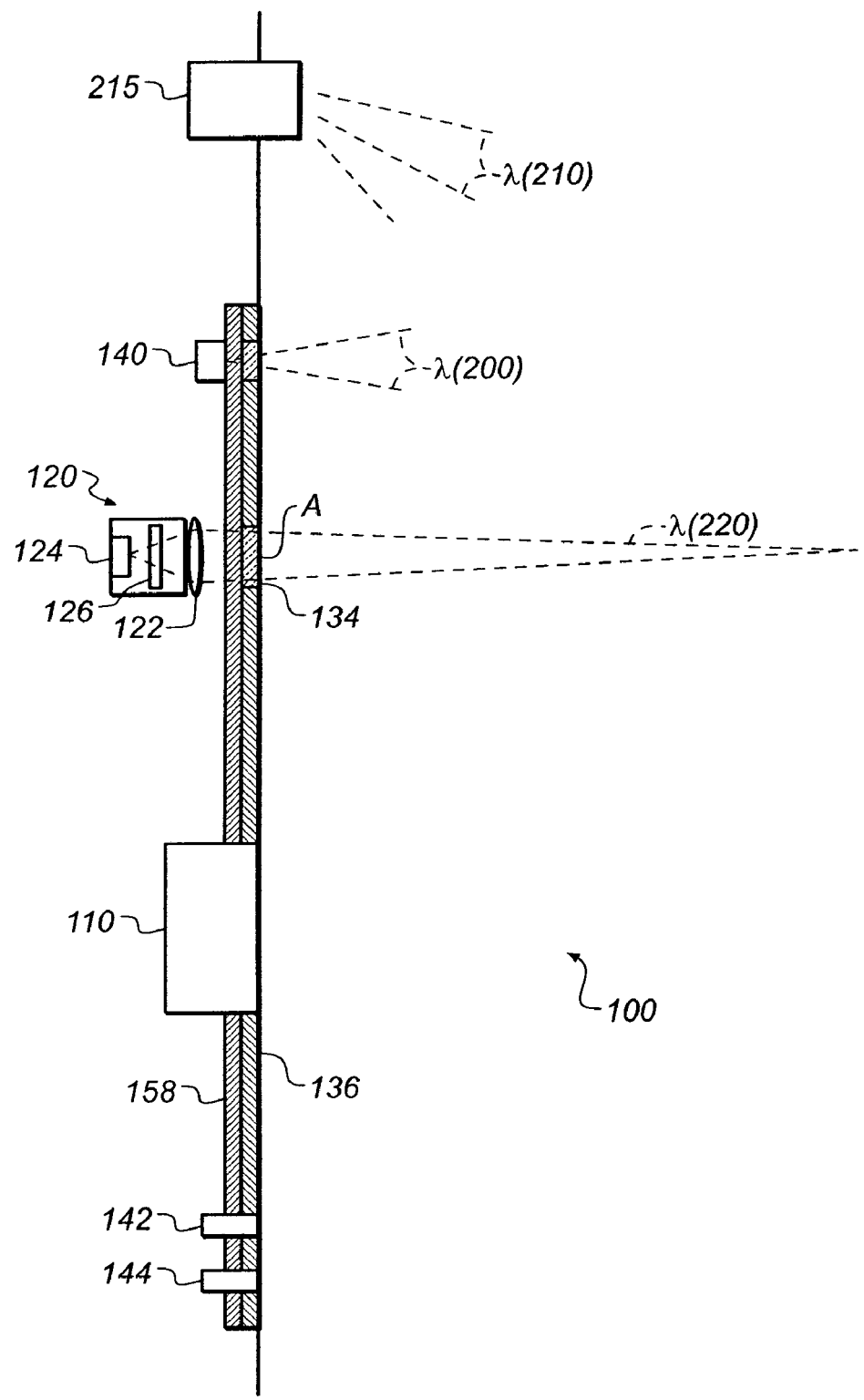
Figure 3:
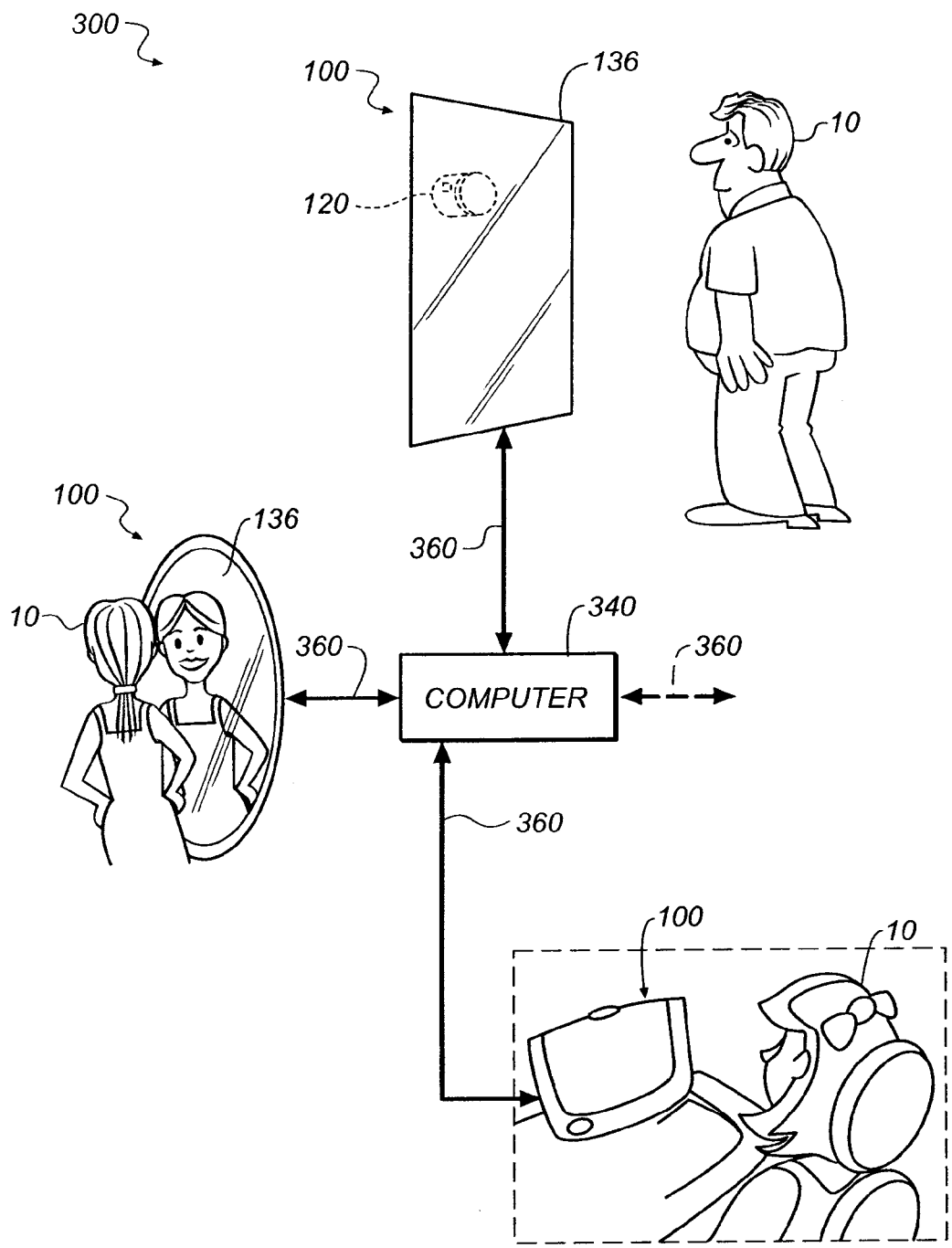
FIG. 3 is an illustration depicting the present invention configured as a network.
Figure 8A:
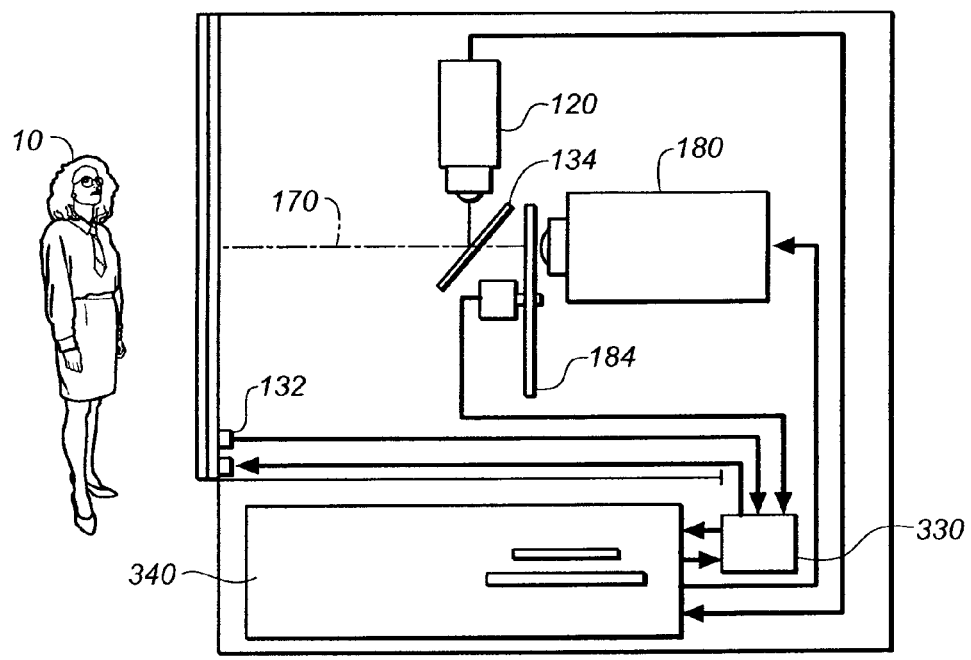
FIGS. 8a and 8b depict alternate constructions for an integrated imaging and capture device, based on prior art designs that can be utilized by the system of the present invention.

Thus far, the electronic imaging device 100 has been generally described as an apparatus with one or more cameras 120 mounted at the top of a computer or television monitor (per FIG. 1) or with one or more cameras 120 imbedded behind a mirror (per FIGS. 2a and 2b). There are other potential constructions however. As a first alternate example, there are many prior art video-conferencing systems that constitute a display that sees, wherein a camera 120 and a display 110 are imbedded behind a flickering screen or around a partially reflecting mirror. For example, as shown in FIG. 8a, a prior art potential electronic imaging device 100, which is described in commonly assigned U.S. Pat. No. 7,042,486, entitled "Image capture and display device" by Manico et al., includes a camera 120 and a projector 180, and a flickering or switching screen 132. In this system, a semi-transparent (partially silvered) mirror 134 is used as a beamsplitter, so that camera 120 and an image display projector 180 share a common optical axis 170 to the switching screen 132. A shutter 184 modulates the projector 180 to block light from reaching the screen during a portion of each frame time corresponding to an image capture by camera 120. The shutter 184 is synchronized with the switching screen 132, such that the shutter's light transmitting state corresponds to the diffusing state of the switching screen 132, and the image provide by projector 180 is displayed at switching screen 132. Whereas, the shutter's opaque position corresponds to the light transmitting state of switching screen 132. In that case cameras 120 peers through the switching screen 132 at a subject 10.

In traditional video-conferencing applications, eye contact with minimal parallax error is of utmost importance. Although eye contact can be useful in certain applications of the present invention, it is not a necessary feature. The traditional configurations for eye contact teleconferencing systems are described in a number of patents, including the above Manico '486 patent, and U.S. Pat. No. 5,639,151 entitled "Pass-through reflective projection display" and U.S. Pat. No. 5,777,665 entitled "Image blocking teleconferencing eye contact terminal", both to McNelley, et al.; and U.S. Pat. No. 5,194,955 entitled "Video telephone" to Yoneta et al., for example. As illustrated by the configuration of FIG. 8a, these traditional video-conferencing systems, which are burdened with partially silvered mirrors and beam splitters, are typically bulky, particularly in the depth direction. Additionally, the currently commercialized products using this general construction are targeted to the corporate executive market rather than consumer markets.

Figure 8B:
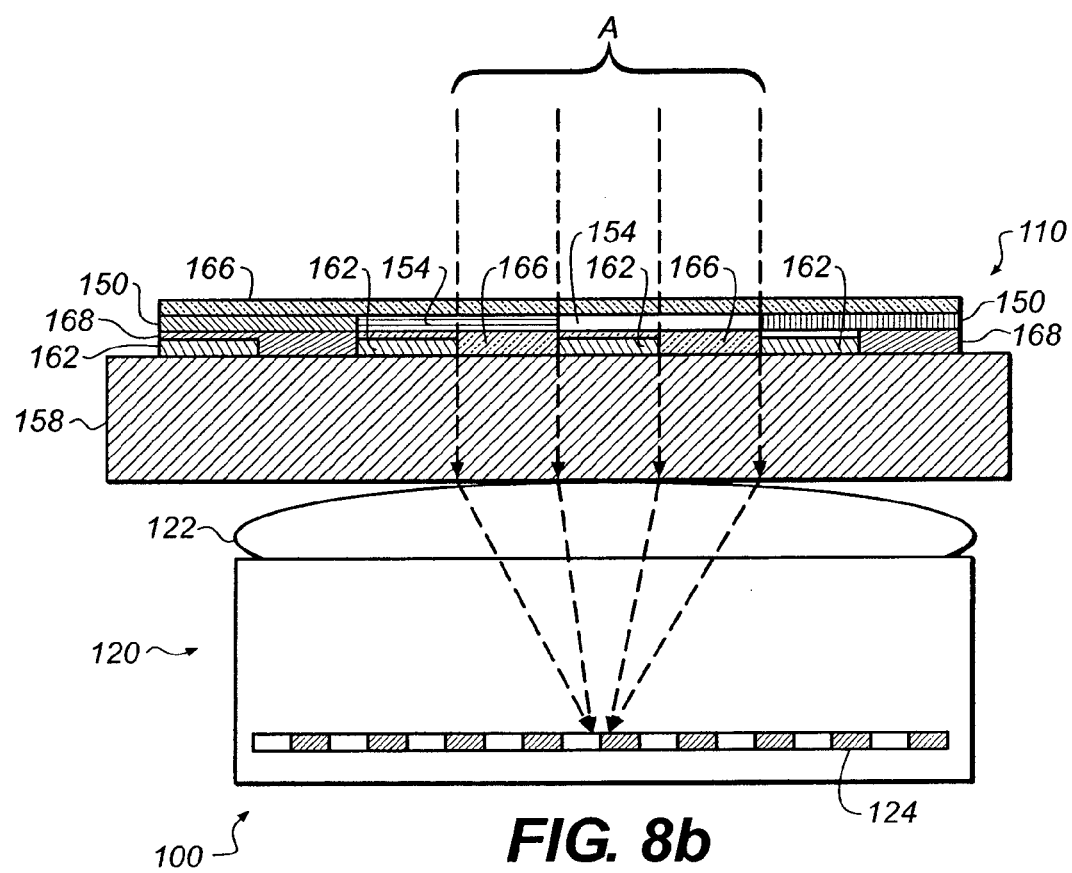

As an alternative approach for providing a display that sees, various parties have proposed a closer integration of image display and sensing components. As one example, illustrated in FIG. 8b, and described in commonly assigned U.S. patent application Ser. No. 11/555,822, by Kurtz et al., and entitled "An Integrated Display Having Multiple Capture Devices", an electronic imaging device 100 with pixel integrated image display and image capture is shown. This device basically includes a camera 120 that peers through a display 110 that includes a configuration of partially transparent pixels. In particular, electronic imaging device 100 includes display pixels 150 and window elements 154 formed on a substrate 158, with patterned thin film electronic components 162 providing control signals and drive current. A pattern of reflective electrodes 168 and transparent electrodes 166 can be used to bring signals and power to each pixel. Some pixels (the window pixels or elements 154) have transparent electrodes 166 both top and bottom, while the normal display pixels 154 have reflective electrodes 168 on the bottom side. The display and window pixels can be white light emitters, or color specific (red, green and blue) light emitters, fabricated with for example, organic light emitting diode (OLED) or polymer light emitting diode (PLED) technologies. An ensemble of partially transparent pixels (window elements 154) is used to form one or more apertures A, that a camera 120 sees through. Although there are potential image artifacts, such as a screen door effect, that can effect the captured image quality, camera 120 can generally focus and function in a normal way. As the camera 120 is closer to the front display surface, this configuration is much more compact than that of FIG. 8a, and is closer structurally to the electronic imaging device 100 shown in FIGS. 2a and 2b. This integrated approach can be particularly useful in the case that the display 110 functions as computer or television monitor, as is generally depicted in FIG. 1. The FIG. 8b approach can basically enable a compact integrated electronic imaging device 100, in which the camera 120 is embedded behind the display 110, rather than positioned off to a side. Thus, improved eye contact imaging is obtained, which can enhance the scleral-based image normalization process, as well as some wellness parameter measurements and assessments.

The present invention has been previously described as typically including an electronic imaging device 100 which includes a camera 120 and a display 110, various sensors, controller 330, and a computer 340 and memory 345, which together support a variety of databases, image processing electronics 320, and inference engine 400. Considering the privacy issues, it can be anticipated that some consumers would prefer that the inference engine 400 and these various databases, including the semantics database 430, the privacy settings database 440, and the wellness parameters database 440, would exist within their residence. However, it can also be anticipated that some consumers would want these data periodically stored in a secure site off their own premises, which can be accomplished by a secure data transfer through the network 360 (which can include the Internet) to an entity specializing in retaining such data.

In a broader context, the assignee of the present invention could operate a business in which the physiological monitoring systems 300, assembled with a variety of OEM and assignee provided components, are sold directly, or indirectly, to consumers (users 10). Various third party providers can be enabled to utilize or interface with the systems on behalf of the consumers. For example, data on new or current prescriptions for medications can be passed from a pharmacy or physician's office, to the semantics database 430 of a system owned by a given consumer. A third party entity can manage the secure data transfer and interface from the pharmacy to the system of a given user 10, and provide any related wellness parameters 410. Likewise, external parties can provide other wellness or set-up data, including wellness parameters 410, to one or more user's systems. A third party can also provide additional analysis modules or extensions for the inference engine 400, which a user 10 can choose to purchase. Alternately, a third party can operate an enhanced inference engine 400 which the user 10 can agree to have their data uploaded to, so as to access enhanced analysis capabilities. For example, the local (at the user's site) inference engine 400 might only complete an initial trend or change analysis. A remote inference engine 400 can then perform a more complete analysis, with interaction with a third party health database 460. Thus, a third party can also maintain and update health databases 460. Again, a given user 10 can potentially choose to obtain such health databases from a third party provider, for local use on the system 300 of the given user 10. Alternately, the given user can have their data uploaded to a third party to gain the benefits of an enhanced health database 460 maintained by the third party. Although the physiological monitoring system 300 is intended to enable the capture and analysis of well-being and health data, it is not intended to necessarily be a diagnostic system. As one approach to diagnostic results, third party providers can also enable medical diagnosis to the consumers, either locally (through extensions to the system) or remotely, depending on the complexities of the diagnostic analysis, associated legalities, and the acceptance of the consumers. Third party participants can also provide health related advertising to the users via this system. In summary, the physiological monitoring system 300 includes a combination of elements, such as a computer, data storage, software, databases, and perhaps a server, which can reside locally (at the residence), or at a remote party, in various combinations, depending on the business models of the entities involved, as well as the preferences of the consumers (users 10) involved.

The invention has been described in detail with particular reference to certain preferred embodiments thereof, but it will be understood that variations and modifications can be effected within the spirit and scope of the invention. As one example, the present invention for physiological monitoring system 300 has been described as employing a structure of various databases (wellness database 420, semantics database 430, privacy settings database 440, capture parameters database 450 and health database 460). Although the physiological monitoring system 300 needs to manage data for wellness, privacy, semantics, image capture, and health, it is noted that other approaches and combinations for data management beside the above-described databases can be used. Likewise, physiological monitoring system 300 has been described as employing various processes for image capture, image capture quality specification, image normalization, image data assessment, and image data reporting. However, other equivalent methods, and changes in the order thereof, can be used to accomplish the goals of the present invention. The physiological monitoring system 300 has also been described relative to its application in residential environments, but the system can be used in the described form, or a modified form, in other environments for related applications. For example, the system, or variants thereof, can be used in physician's offices and clinics, long-term care facilities, educational facilities, corporate offices, or for drug-testing and behavioral therapeutics applications. The application of physiological monitoring system 300 can also be extended for the use in monitoring the well-being of family pets. It should be understood that the various drawing and figures provided within this invention disclosure are intended to be illustrative of the invention and are not to-scale engineering drawings.

PARTS LIST

A Aperture
10 User (or subject)
20 human body
25 face
30 eye
32 sclera
34 iris
36 pupil
40 skin
50 torso
60 mouth
65 hair
100 electronic imaging device
110 display
120 camera
122 imaging lens
124 sensor array
126 spectral filter
132 switching screen
134 semi-transparent mirror
136 mirror
140 ambient light detector
142 motion detector
144 secondary detector
150 display pixels
154 window elements
158 substrate
162 thin film electronic components
166 transparent electrode
168 reflective electrode
170 optical axis
180 projector
184 shutter
200 ambient light
210 illumination light
215 illumination light source
220 capture light
230 display light
300 physiological monitoring system
310 Image capture system
320 image processing electronics
310 system controller
340 computer
345 data storage (or memory)
350 alert signal
355 communications controller
360 network
365 reference image
367 reference feature
370 visual journal
400 inference engine
402a, 402b, 402c, 402d steps (for wellness inference or assessment)
410 wellness parameters
415 capture parameters
420 wellness parameters database
430 semantics database
440 privacy settings database
450 capture parameters database
460 health database
500 image normalization process
502a, 502b, 502c steps (for the normalization process)
510 subject identification process
512 sense an individual step
515 user tracking process
520 auto-setup process
522a, 522b, 522c, 522d, 522e, 522f steps (for auto-setup process)
540 initial imaging process
550 well-being image capture process
552a, 552b, 552c steps (for well-being data capture)

The invention claimed is:
1. A method for providing normalized physiological monitoring data of an individual with a measure of the quality of the normalization, comprising;
providing a reference feature based on a physiological attribute of the individual for which an attribute value can be determined;

unobtrusively capturing physiological monitoring data for the individual during a series of capture events and determining the capture conditions present during each capture event;

detecting the presence of the reference feature in the series of captured physiological monitoring data and determining associated attribute values for each capture event;

normalizing the captured physiological monitoring data from each capture event according to differences in the attribute values associated with each event and previously calculated attribute values; and calculating normalization confidence values for the individual at the series of capture events, based on capture conditions, normalization transforms, or semantic data, wherein the confidence values statistically measure the quality of the normalization.

2. The method as in claim 1 wherein the semantic data related to the individual, that can affect the quality of the normalization, includes the time of day of a capture event, the use of cosmetics, or the tiredness of the individual.

3. The method as in claim 1 wherein the normalization confidence values are tracked over multiple capture events to monitor changes in normalization quality over time.

4. The method as in claim 1 further comprising determining if valid wellness parameters can be derived based on the normalization confidence values, wherein the wellness parameters are associated with the physiological attributes being monitored.

5. The method as in claim 1 wherein the attribute values or normalization transforms are obtained by RGB or spectral color measurements of: the sclera, the skin, the tongue, the ambient light, or the capture light.

6. The method as in claim 1 wherein the physiological monitoring data is obtained by image capture, audio capture or multi-spectral capture.

7. The method as in claim 6 wherein the capture conditions are derived as capture parameters from one or more captured images acquired during a capture event.

8. The method as in claim 6 wherein the face of the individual in the captured images is normalized in each image according to color attributes of one or more facial reference features of the individual.

9. The method as in claim 6 wherein the face of the individual in the captured images is normalized based on the spatial disparity between two or more facial reference features of the individual.

10. The method as in claim 9 wherein the captured images of the individual are normalized based on the spatial disparity between corresponding features of both eyes of the individual.

11. The method as in claim 6 wherein the captured images of the individual are normalized to provide changes in the size or orientation or combinations thereof of the image of the individual.

12. The method as in claim 6 wherein the audio capture is normalized to reduce the noise associated with voice capture under variable capture conditions.

13. The method as in claim 1 wherein the physiological attributes and associated reference features include color, size, weight, posture, gait, motion, or voice.

14. The method as in claim 1 wherein the reference features are related to physiological attributes of one or both eyes, the skin, the tongue, one or more teeth or combinations thereof.

15. A method for providing normalized images of an individual from a physiological monitoring system comprising;

providing a reference feature based on the sclera of one or more eyes of the individual from which color attribute values can be determined capturing an image of the individual during a first capture event and determining the presence of a reference feature in the captured image and determining a first attribute value;

capturing an image of the individual during a second capture event and determining the presence of the reference feature in the second captured image and determining a second attribute value; and normalizing the second captured image according to differences between the first and second attribute values.

16. The method of claim 15 wherein the sclera feature is the average color value excluding the blood vessels of at least one eye of the individual.

17. The method of claim 15 wherein the differences in sclera color are due to changes in the capture lighting conditions at the time of capture.

* * * * *